(12) United States Patent
Yehiely et al.

(10) Patent No.: US 7,749,977 B2
(45) Date of Patent: Jul. 6, 2010

(54) THERAPEUTIC MODULATION OF THE FAS PATHWAY

(75) Inventors: Fruma Yehiely, Chicago, IL (US); Louis Deiss, Chicago, IL (US); Paz Einat, Nes Zionna (IL)

(73) Assignee: Quark Pharmaceuticals, Inc., Fremont, CA (US)

( * ) Notice: Subject to any disclaimer, the term of this patent is extended or adjusted under 35 U.S.C. 154(b) by 454 days.

(21) Appl. No.: 11/586,021

(22) Filed: Oct. 24, 2006

(65) Prior Publication Data

US 2007/0042418 A1 Feb. 22, 2007

Related U.S. Application Data

(63) Continuation of application No. 10/704,112, filed on Nov. 7, 2003, now abandoned, which is a continuation-in-part of application No. 09/499,553, filed on Feb. 7, 2000, now abandoned, which is a continuation-in-part of application No. 09/284,782, filed as application No. PCT/US97/20989 on Nov. 12, 1997, now Pat. No. 6,057,111.

(51) Int. Cl.
*A61K 31/70* (2006.01)
*C07H 21/02* (2006.01)
(52) U.S. Cl. ........................................ 514/44; 536/24.5
(58) Field of Classification Search ........................ None
See application file for complete search history.

(56) References Cited

U.S. PATENT DOCUMENTS

| 5,604,118 | A | 2/1997 | Giri et al. |
| 5,612,180 | A | 3/1997 | Brown et al. |
| 7,056,704 | B2 * | 6/2006 | Tuschl et al. ............... 435/91.1 |
| 2004/0219569 | A1 | 11/2004 | Yehiely et al. |
| 2006/0069056 | A1 | 3/2006 | Feinstein et al. |

FOREIGN PATENT DOCUMENTS

| WO | WO-01/94629 A2 | 12/2001 |
| WO | WO 2006/128041 A2 | 11/2006 |
| WO | WO 2006/128041 A3 | 11/2006 |

OTHER PUBLICATIONS

Shen et al (FEBS letters 539: 111-114 (2003).*
Xia et al., Nature Biotechnology 20:1006-1010 (2002).*
Reich et al., Molecular Vision 9:210-216 (2003).*
Sorensen et al. (J.Mol.Biol. 327:761-766 (2003).*
Lewis et al., Nature Genetics 32:107-108 (2002).*
Simeoni et al., Nucleic Acids Research 31, 11:2717-2724 (2003).*
Lewis et al (Meth. Enzymol. 392, 336-350, 2005).*
Dykxhoorn et al (Ann. Rev. Biomed. Eng. 8: 377-402, 2006).*
Caplen (Expert Opin. Biol. Ther. 2003, vol. 3, pp. 575-586, 2003).*
Coburn et al. 2003, Journal of Antimicrobial Chemotherapy. vol. 51, pp. 753-756.*
Agami et al. 2002 Current Opinion in Chemical Biology. vol. 6, pp. 829-834).*
Opalinska et al. (Nature Reviews Drug Discovery, 2002, vol. 1, pp. 503-514).*
Check (Nature, 2003, vol. 425, pp. 10-12).*
Zhang et al (Current Pharmaceutical Biotechnology 2004, vol. 5, pp. 1-7).*
Heidenreich (Current Pharmaceutical Biotechnology 5: 349-354, 2004).*
Izquierdo (Cancer Gene Therapy, 12: 217-227, 2005).*
Ogasawara (Nature 364: 806-809, 1993).*
Vahdat et al (Blood 84: 3843-3849, 1994).*
Wang et al (Proc. Nat. Acad. Sci. USA 104(49): 19589-19594, 2007).*
Venditti et al (Ann. Hematol. 66: 59-60, 1993).*
Nakanishi et al (Gene Therapy 10: 434-442, Mar. 2003).*
Kotlo et al (Oncogene 22: 797-806 Feb. 13, 2003).*
T. A. Holzmayer, D.G. Pestov, and I.B. Roninson, Isolation of Dominant Negative Mutants and Inhibitory Antisense RNA Sequences by Expression Selection of Random DNA Fragments, Nucleic Acids Res., vol. 20, No. 4, pp. 711-717 (1992).
A.V. Gudkov, Isolation of Genetic Suppressor Elements, Inducing Resistance to Topoisomerase II-Interactive Cytotoxic Drugs, from Human Topoisomerase II cDNA, *Proc. Natl. Acad. Sci.*, vol. 90, pp. 3231-3235 (1993).
A.V. Gudkov et al., Cloning Mammalian Genes by Expression Selection of Genetic Suppressor Elements: Association of Kinesin with Drug Resistance and Cell Immortalization, *Proc. Natl. Acad. Sci.*, vol. 91, pp. 3744-3748 (1994).
I.B. Roninson et al., Genetic Suppressor Elements: New Tools for Molecular Oncology—Thirteenth Cornelius P. Rhoads Memorial Award Lecture, *Cancer Res.*, vol. 55, pp. 4023-4028 (1995).
V.S. Ossovskaya et al., Use of Genetic Suppressor Elements to Dissect Distinct Biological Effects of Separate p53 Domains, *Proc. Natl. Acad. Sci.*, vol. 93, pp. 10309-10314 (1996).
A.V. Gudkov and I.B. Roninson, Isolation of Genetic Suppressor Elements (GSEs) from Random Fragment cDNA Libraries in Retroviral Vectors, *Methods Mol. Biol.* vol. 69, pp. 221-240 (1997).
M.R. Abedi, G. Caponigro, and A. Kamb, Green Fluorescent Protien as a Scaffold for Intracellular Presentation of Peptides, Nucleic Acids Res., vol. 26, No. 2, pp. 623-630 (1998).

(Continued)

*Primary Examiner*—Richard Schnizer
(74) *Attorney, Agent, or Firm*—John P. White; Cooper & Dunham LLP

(57) ABSTRACT

A method for the identification of genes that are essential for the maintenance of specific cell phenotypes is disclosed. The method includes the initial step of identifying a cell type with a phenotype of interest. Gene inactivation is performed on an aliquot of cells of the cell type of interest. Selection is then performed to an aliquot of the cell culture to which gene inactivation has been applied. Cells which continue to maintain the phenotype following gene inactivation have not had the gene of interest inactivated whereas cells in which genes necessary for maintaining the phenotype have been inactivated have been lost. Utilizing subtraction analysis between treated and untreated aliquots the gene in the cells which has been inactivated that affects the phenotype of interest is identified. Genes that are identified by the method are also disclosed as well as antibodies directed against the gene product of the identified genes. Further a customized kit for the practice of the gene identification method is also disclosed.

5 Claims, 12 Drawing Sheets

OTHER PUBLICATIONS

W.M. Gallagher et al., Identification of p53 Genetic Suppressor Elements which Confer Resistence to Cisplatin, *Oncogene* vol. 14, pp. 185-193 (1997).

G. Caponigro et al., Transdominant Genetic Analysis of a Growth Control Pathway, *Proc. Natl. Acad. Sci.*, vol. 95, pp. 7508-7513 (1998).

I.B. Roninson et al., Isolation of Altered-Function Mutants and Genetic Suppressor Elements of Multidrug Transporter P-glycoprotien by Expression Selection from Retroviral Libraries, *Methods Enzymol.*, vol. 292, pp. 225-249 (1998).

Smith et al., Genetic footprinting: A genomic strategy for determining a gene's function given its sequence, *Proc. Natl. Acad. Sci. USA*, vol. 92, pp. 6479-6483 (1995).

Adi Kimchi, Cytokine Triggered Molecular Pathways That Control Cell Cycle Arrest, *Journal of Cellular Biochemistry*, vol. 50, pp. 1-9 (1992).

Deiss et al., Cathepsin D protease mediates programmed cell death induced by interferon-γ, Fas/APO-1 and TNF-α, *The EMBO Journal*, vol. 15, No. 15, pp. 3861-3870 (1996).

Lisitsyn et al., Comparative genomic analysis of tumors: Detection of DNA losses and amplification, *Proc. Natl. Acad. Sci. USA*, vol. 92, pp. 151-155, (1995).

Yancopoulos et al., Isolation of coordinately regulated genes that are expressed in discrete stages of B-cell development, *Proc. Natl. Acad. Sci. USA*, vol. 87, pp. 5759-5763 (1990).

Lee et al., Positive selection of candidate tumor-suppressor genes by subtractive hybridization, Proc. Natl. Acad. Sci. USA, vol. 88, pp. 2825-2829 (1991).

Diatchenko et al., Suppression subtractive hybridization: A method for generating differentially regulated or tissue-specific cDNA probes and libraries, *Proc. Natl. Acad. Sci. USA*, vol. 93, pp. 6025-6030 (1996).

Hubank et al., Identifying differences in mRNA expression by representational difference analysis of cDNA, *Nucleic Acids Research*, vol. 22, No. 25, pp. 5640-5648 (1994).

Braun et al., Identification of Target Genes for the Ewing's Sarcoma EWS/FLI Fusion Protein by Representational Difference Analysis, *Molecular and Cellular Biology*, vol. 15, No. 8, pp. 4623-4630 (1995).

Gudkov et al., Isolation of genetic suppressor elements, inducing resistance to topoisomerase II-interactive cytotoxic drugs, from human topoisomerase II cDNA, *Proc. Natl. Acad. Sci. USA*, vol. 90, pp. 3231-3235 (1993).

Gudkov et al., Cloning mammalian genes by expression selection of genetic suppressor elements: Association of kinesin with drug resistance and cell immortalization, *Proc. Natl. Acad. Sci. USA*, vol. 91, pp. 3744-3748 (1994).

Kissil et al., Isolation of DAP3, a Novel Mediator of Interferon-γ-induced Cell Death, *The Journal of Biological Chemistry*, vol. 270, No. 46, pp. 27932-27936 (1995).

Beyaert, R. et al., Casein Kinase-I Phosphorylates the p75 Tumor Necrosis Factor Receptor and Negatively Regulates Tumor Necrosis Factor Signaling for Apoptosis, Journal of Biological Chemistry, vol. 270, No. 40, pp. 23293-23299 (1995).

Deiss et al., Identification of a novel serine/threonin kinase and a novel 15-kd protein as potential mediators of the gamma interferon-induced cell death. Genes & Development. 1995, 9:15-30.

Deiss et al., A generic tool used to identify thioredoxin as a mediator of a growth inhibitory signal. Science. Apr. 1991, 252: 117-120.

Klickstein. "Production of a subtracted cDNA library," Unit 5.8B in: Current Protocols in Molecular Biology. Ausubel et al. (Eds.) John Wiley & Sons, Inc. 1992, pp. 5.8.9-5.8.15.

Lecine, P. et al., Mice Lacking Transcription Factor NF-E2 Provide In Vivo Validation of the Proplatelet Model of Thrombocytopoiesis and Show a Platelet Production Defect That Is Intrinsic to Megakaryocytes, Blood, vol. 92, No. 5, pp. 1608-1616 (1998).

Listsyn et al., Cloning the Differences Between Two Complex Genesomes. Science. Feb. 1993, 259:946-951.

McCarthy, J. et al., RIP2 Is a Novel NF-κB-activating and Cell Death-inducing Kinase, Journal of Biological Chemistry, vol. 273, No. 27, pp. 16968-16975 (1998).

Morrow, C.S., et al., Coordinated Action of Glutathione S-Transferases (GSTs) and Multidrug Resistance Protein 1 (MRP1) in Antineoplastic Drug Detoxification, Journal of Biological Chemistry, vol. 273, No. 32, pp. 20114-20120 (1998).

Smith, V., et al., Functional Analysis of the Genes of Yeast Chromosome V by Genetic Footprinting, Science, vol. 274, pp. 2069-2074 (1996).

Wang, Y. et al., The Identification of a Cis-element and a Trans-acting Factor Involved in the Response to Polyamines and Polyamine Analogues in the Regulation of the Human Spermidine/Spermine N1-Acetyltransferase Gene Transcription, Journal of Biological Chemistry, vol. 273, No. 51, pp. 34623-34630 (1998).

International Search Report issued by the International Searching Authority (ISA/US) on Jan. 8, 2009 in connection with International Application No. PCT/IL08/00391.

Written Opinion issued by the International Searching Authority (ISA/US) on Jan. 8, 2009 in connection with International Application No. PCT/IL08/00391.

* cited by examiner

FIG. 5B

THERAPEUTIC MODULATION OF THE FAS PATHWAY

CROSS-REFERENCE TO RELATED APPLICATIONS

This application is a continuation of U.S. patent application Ser. No. 10/704,112, filed Nov. 7, 2003, now abandoned, which is a continuation-in-part of U.S. patent application Ser. No. 09/499,553, filed Feb. 7, 2000, now abandoned, which is a continuation-in-part of U.S. patent application Ser. No. 09/284,782, filed Jul. 6, 1999, now U.S. Pat. No. 6,057,111, issued May 12, 2000, which is a §371 National Phase of PCT International Serial Number No. PCT/US97/20989, filed Nov. 12, 1997, all of which are hereby incorporated by reference in their entireties into this application.

BACKGROUND OF THE INVENTION

1. Field of the Invention

The present invention relates to a method of identifying genes, specifically genes that maintain specific cell phenotypes.

2. Description of Related Art

There are methods available to isolate and identify specific genes. However these methods are not efficient and rapid. Applicant has previous disclosed the Technical Knock Out (TKO) selection method which has the advantage of rapid isolation of genes that inhibit proliferation in a specified restrictive environment [Deiss and Kimchi, 1991; Deiss et al, 1995; Kissil et al, 1995; Deiss et al, 1996]. However, this method has the limitation of requiring a phenotype that can be efficiently selected against, such as a cell growth arrest or cell killing phenotype.

Recently Smith et al [1995] and U.S. Pat. No. 5,612,180 have described a method called genetic footprinting to identify genes. The method involves mutagenesis of potentially large numbers of genes followed by a genetic selection of the cells containing the mutated genes. This is followed by retrospective analysis of the effect of individual gene inactivation on the behavior cells containing these inactivations. From this information new genes are determined. This method has significant disadvantages for large scale gene identification. The genetic footprinting method involves mutagenesis by gene insertion and because of this requires a haploid target which imposes a limitation on the method. Second, the method of determining the effect of each gene inactivation on the fitness of the cells containing the mutation involves a PCR amplification of the target gene which requires prior knowledge of the nucleotide sequence of all the target genes that will be studied which limits the gene base which can be searched.

It would be useful to have a method which does not require a haploid target and does not require a known sequence.

It would be useful to have a rapid method which can identify genes to be isolated that are essential for the maintenance of specific cell phenotypes where positive selection exists for the phenotypes. These identified genes are excellent targets for the development of pharmacological inhibitors which would also act clinically to inhibit the specific phenotype. In other words it would be useful to have a tool which can effectively identify pharmacological targets for inhibition of deleterious phenotypes.

SUMMARY OF THE INVENTION

According to the present invention, a method for the identification of genes that are essential for the maintenance of specific cell phenotypes is disclosed.

The method includes the initial step of identifying a cell type with a phenotype of interest. The method allows the phenotype of interest to be phenotypes relating to growth, phenotypes relating to release of factors and phenotypes relating to other basic cell functions.

Gene inactivation is performed on an aliquot of cells of the cell type of interest. Possible methods of gene inactivation include Genetic Suppressor Element (GSE) inactivation, Random Homozygous Knock-Out (RHKO) inactivation, Technical Knock Out (TKO) inactivation, and RNAi.

Selection is then performed on an aliquot of the cell culture to which gene inactivation has been applied. The selection includes manipulations that test the ability of cells to survive under specific culture conditions, ability to express a specific factor, changes in cell structure, or differential gene expression.

Cells which continue to maintain the phenotype following gene inactivation have not had the gene of interest inactivated whereas cells in which genes necessary for maintaining the phenotype have been inactivated have been lost. Utilizing subtraction analysis between treated and untreated aliquots the gene in the cells which has been inactivated that affects the phenotype of interest is identified. The subtraction analysis can include the methods of differential display, representational differential analysis (RDA), suppressive subtraction hybridization (SSH), serial analysis of gene expression (SAGE), gene expression microarray (GEM), nucleic acid chip technology, or direct sequencing.

The invention further discloses the genes that are identified by the method of the present invention and for antibodies directed against the gene product of these identified genes. The present invention also provides for a customized kit to practice the method of the present invention.

DESCRIPTION OF THE DRAWINGS

Other advantages of the present invention will be readily appreciated as the same becomes better understood by reference to the following detailed description when considered in connection with the accompanying drawings wherein:

FIGS. 5A-D show the effect of the AHM method on cell proliferation; A. shows how anti-sense Nrf2 sensitizes HeLa cells to Fas induced PCD; B. shows the levels of expression of Nrf2; C. shows how Dicumarol sensitizes HeLa cells to Fas induced PCD; D. shows how N-acetyl cysteine protects HeLa cells from Fas induced PCD.

DETAILED DESCRIPTION OF THE INVENTION

Figure 1:
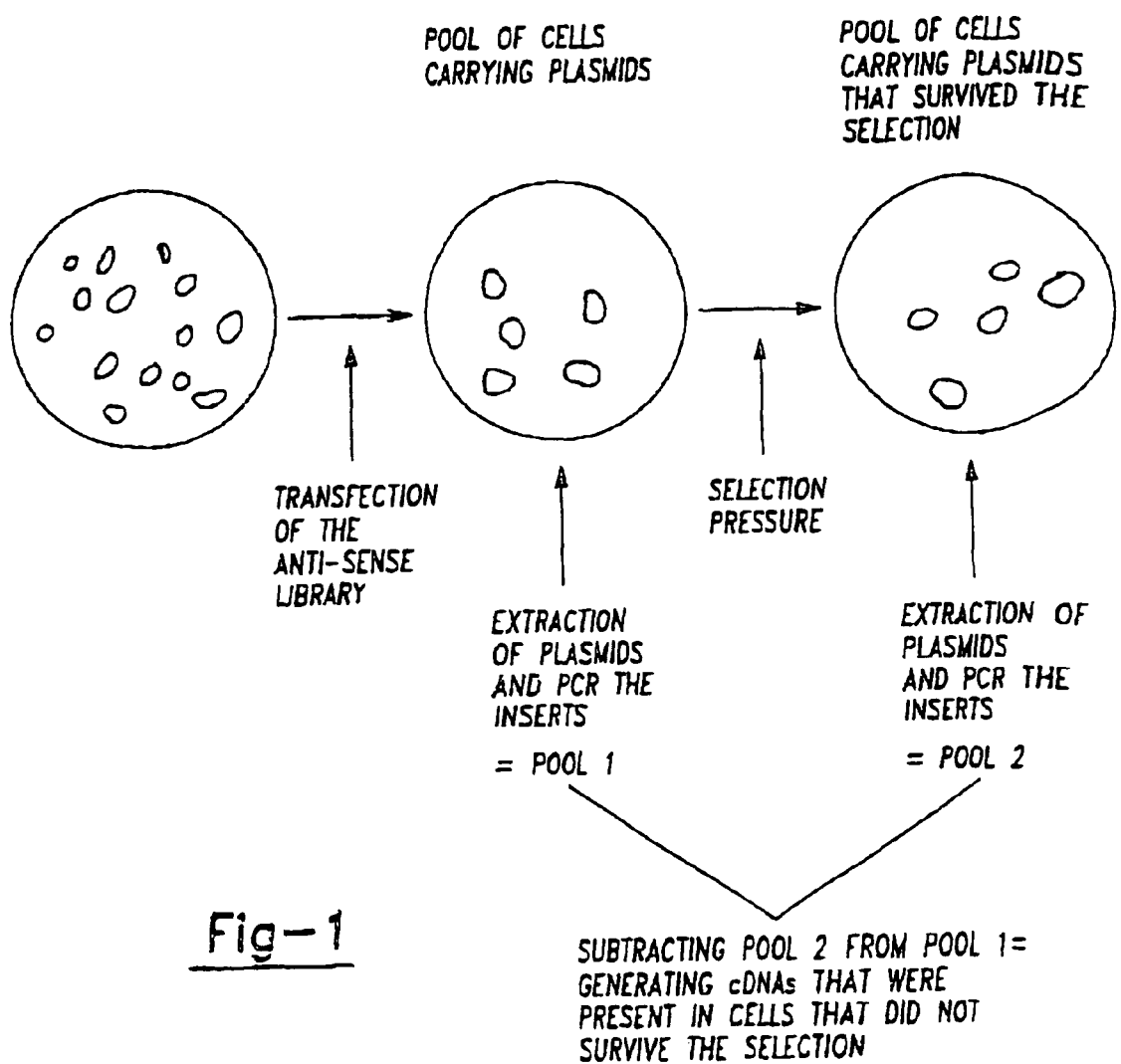
FIG. 1 is a schematic representation of a general outline of the method of the present invention.

According to the present invention, a method for the identification of which genes are essential for the maintenance of a specific cell phenotype is disclosed. Phenotypes that can be studied are those for which changes can be monitored in either haploid or diploid cells. The method requires two general steps.

The first is the inactivation of genes in the cell by any method known in the art and then in the second applying positive selection for the phenotype of interest followed by the identification via a subtraction analysis of the gene in the cells which has been inactivated that affects the phenotype of interest. By this method, a collection of genes that are essential for the maintenance of a specific phenotype are identified at the conclusion of the procedure.

The invention further discloses the genes that are identified by the method of the present invention and for antibodies directed against the gene product of these identified genes.

Briefly, the method includes initially the identification of a cell type for which genes controlling its phenotype are needed. Once the cell type has been identified, where required for the method an expression cDNA library is constructed of the cells as they are expressing the phenotype.

Several methods are available for the gene inactivation step: Genetic Suppressor Element (GSE) [Holzmeyer et al, 1992; Roninson et al, 1995; Gudkov et al, 1994], Random Homozygous Knock-Out (RHKO) [Li and Cohen, 1996], Technical Knock Out (TKO), [described herein above] and RNAi or siRNA. Of these methods the TKO and RNAi methods are adaptable to the second step of the present method as described herein below in Example 1.

RNAi, or dsRNA is a phenomena which was first observed in plants, whereby attempts to create transgenic plants often resulted in loss of expression of the transgene. The insertion of multiple copies of the transgene into the plant genome was known to often result in the inactivation of some or all of the copies of the transgene.

Suppression of gene expression as a result of the introduction of an exogenous copy of the gene or part of the gene was reported in plants as early as 1990 (Napoli et al., The Plant Cell 2, 279-289 (1990); van der Krol et al., The Plant Cell 2, 291-299 (1990)). In addition, a phenomena sometimes named "quelling" was observed in plants, whereby transformation with homologous sequences (not necessarily full or partial genes) resulted in transient inactivation of gene expression (Romano and Macino, Molecular Microbiology 6(22): 3343-3353 (1992)).

dsRNA was subsequently found to cause genetic interference with the endogenous counterpart in plants, *C. Elegans* (Fire et al., Nature 391, 806-811 (1998)) and *Drosophila* (Kennerdell and Carthew, Cell 95, 1017-1026 (1998)), more effectively than the antisense RNA of the gene alone. The mechanism by which this silencing occurred was said to possibly be linked to both DNA methylation and antisense RNA (Wassenegger and Pelissier, Plant Molecular Biology 37: 349-362 (1998)). As a minimal number of dsRNA molecules proved sufficient to affect the gene silencing, it was proposed that a catalytic component may be involved in the silencing process (see Fire et al., above). Montgomery and Fire (TIG 14,7: 255-258 (1998)) further proposed a model mechanism which was thought to account for the inhibitory effects, suggesting that suppression is often carried out via dsRNA, which may be formed unintentionally in experiments such as the introduction of a transgene. It was suggested that dsRNA may cause the early degradation of the endogenous mRNA. Several additional models were proposed for the wide array of suppression phenomena observed (Fire, TIG 15, 9: 358-363 (1999)).

dsRNA was also found to be an effective tool in silencing genes in mammals (Wianny and Zernicka-Goetz, Nature Cell Biology 2, 70-75 (2000)).

Further elucidation of the mechanism of RNA interference occurred when Zamore et al. (Cell 101, 25-33 (2000)) found that dsRNA directs the sequence-specific degradation of mRNA through an ATP dependent mechanism uncoupled from mRNA translation; it was observed that both strands of the dsRNA are processed to RNA segments of 21-23 nucleotides long; the targeted mRNA is not required to affect this process. Additional evidence that the silencing is in fact mediated by small RNAs of 20-25 nucleotides has emerged (Hamilton and Baulcombe, Science 286: 950-952 (1999); Elbashir et al., Nature 411: 494-498 (2001)).

Taken together, the observations presented in the growing body of research into this topic suggests that RNAi is an ancient and highly conserved mechanism by which organisms protected themselves against viral infection and various deleterious effects that may be attributed to over-expression of certain genes.

The mechanisms underlying RNAi are reviewed in Hannon, Nature 418: 244-251 (2002), and McManus and Sharp, Nature Reviews (Genetics), 3: 737-746 (2002).

siRNA as a Therapeutic Molecule

Recent studies have suggested that siRNAs may be used as drugs for the silencing of a harmful gene in certain cases. The idea behind this is similar to that of antisense molecules as therapeutic agents. The mechanism of action of antisense RNA and the current state of the art on use of antisense tools is reviewed in Kumar et al (1998): Antisense RNA: function and fate of duplex RNA in cells of higher eukaryotes. *Microbiol Mol Biol Rev.* 1998 December; 62(4):1415-34. There are reviews on the chemical aspects (Crooke, 1995: Progress in antisense therapeutics. *Hematol Pathol.* 1995; 9(2):59-72.; Uhlmann et al, 1990), cellular aspects (Wagner, 1994: Gene inhibition using antisense oligodeoxynucleotides. *Nature.* 1994 Nov. 24; 372(6504):333-5.) and therapeutic aspects (Hanania, et al, 1995: Recent advances in the application of gene therapy to human disease. *Am J Med.* 1995 November; 99(5):537-52; Scanlon, et al, 1995: Oligonucleotide-mediated modulation of mammalian gene expression. *FASEB J.* 1995 October; 9(13):1288-96; Gewirtz, 1993: Oligodeoxynucleotide-based therapeutics for human leukemias. *Stem Cells.* 1993 October; 11 Suppl 3:96-103) of this rapidly developing technology. The use of antisense oligonucleotides in inhibition of various genes has been described in Yeh et al (1998): Inhibition of BMP receptor synthesis by antisense oligonucleotides attenuates OP-1 action in primary cultures of fetal rat calvaria cells. *J Bone Miller Res.* 1998 December; 13(12):1870-9; Meiri et al (1998) Memory and long-term potentiation (LTP) dissociated: normal spatial memory despite CA1 LTP elimination with Kv1.4 antisense. *Proc Natl Acad Sci USA.* 1998 Dec. 8; 95(25):15037-42; Kondo et al (1998): Antisense telomerase treatment: induction of two distinct pathways, apoptosis and differentiation. *FASEB J.* 1998 July; 12(10):801-11; Stix (1998): Shutting down a gene. Antisense drug wins approval. *Sci Am.* 1998 November; 279 (5):46, 50; Flanagan (1998) Antisense comes of age. *Cancer Metastasis Rev.* 1998 June; 17(2):169-76; Guinot et al (1998)

Antisense oligonucleotides: a new therapeutic approach *Pathol Biol* (Paris). 1998 May; 46(5):347-54, and references therein. The methods described therein also apply generally to delivery of siRNAs.

Recently, delivery systems aimed specifically at the enhanced and improved delivery of siRNA into mammalian cells have been developed. Shen et al (FEBS letters 539: 111-114 (2003)) described an adenovirus-based vector which efficiently delivers siRNAs into mammalian cells. Additional detail on viral-based siRNA delivery systems can be found in Xia et al., Nature Biotechnology 20: 1006-1010 (2002); and Reich et al., Molecular Vision 9: 210-216 (2003).

Sorensen et al. (J. Mol. Biol. 327: 761-766 (2003)) devised injection-based systems for systemic delivery of siRNAs to adult mice, by cationic liposome-based intravenous injection and/or intraperitoneal injection.

A system for efficient delivery of siRNA into mice by rapid tail vain injection has also been developed (Lewis et al., nature genetics 32: 107-108 (2002)).

Additionally, the peptide based gene delivery system MPG, previously used for DNA targeting, has been modified to be effective with siRNAs (Simeoni et al., Nuclaic Acids Research 31, 11: 2717-2724 (2003)).

Any method for gene inactivation may be used with existing or later derived methods which can be adapted to work with the second step of the present method.

Following gene inactivation treatment, an aliquot of the treated cells are exposed to a positive selection.

That is, the cells are exposed to conditions requiring/activating the phenotype of interest. A reserved aliquot of the treated cells is not exposed.

Following positive selection, cells which continue to express the desired phenotype remain and those cells which cannot maintain the phenotype are lost. The method then provides for determining the gene that was not expressed in the lost cells by a "subtraction" analysis by any method known in the art, generally utilizing a comparison between the reserved cell aliquot and the cells remaining after selection. It should be noted that many aliquots can be tested and screened. The gene(s) identified is at least one of the genes which controls the phenotype.

The relative abundance of the differences between the "targeted" and "untargeted" aliquots are simultaneously compared using a "subtraction" analysis (differential analysis) technique such as differential display, representational difference analysis (RDA), GEM-Gene Expression Microarrays (Schena et al., 1995; Aiello et al., 1994; Shen et al., 1995; Bauer et al., 1993; Liang and Pardee, 1992; 1995, Liang et al., 1993; Braun et al., 1995, Hubank and Schatz, 1994; U.S. Pat. No. 5,545,531), suppressive subtraction hybridization (SSH) and direct sequencing (W096/17957).

In the preferred method or process the procedure involves the transfection of targets cells with an anti-sense expression library or RNAi library followed by the positive selection of cells which have maintained a specific phenotype in the face of a specific challenge to the phenotype. It should be noted that one construct can be tested or many can be tested simultaneously in this method including over 100,000 constructs from an expression library. Cells in which an anti-sense inactivation has targeted a "sense" gene essential for the selected phenotype will be lost during the selection. Applicants have found that in general one cell has incorporated only one construct.

In this embodiment the next steps are to identify and isolate anti-sense expression vectors that are lost from the cell population due to cell loss during positive selection, that is, that induce a disadvantage in transfected cells during specific, positive selection resulting in the loss of the cell carrying the vector.

These vectors are identified by subtracting the anti-sense expression vectors present after the selection from those present before the selection utilizing the reserved cell aliquot. This difference represents the vectors that express anti-sense against gene(s) that are essential for the maintenance of the selected phenotype.

These vectors are then recloned and sequenced. The identified anti-sense expression vectors are re-tested individually for the ability to inactivate the specific phenotype. With the sequence identified, the sense gene controlling the phenotype of interest can be identified using standard methods known in the art.

More specifically, the first part of the method consists of transfecting a target cell culture aliquot with an anti-sense expression library. The library is generated by cloning a cDNA library in the anti-sense orientation into an expression cassette that will express the anti-sense strand at a high efficiency. The cassette also contains a resistance marker that allows for selection of cells that have been successfully transfected. The cells that are transfected are ones that express a phenotype of interest. The transfection results in a pool of cells that will express anti-sense messages against a large number of the genes expressed in the cell. These anti-sense messages will inactivate the functional expression of the corresponding sense message. This results in a pool of cells "knocked out" for the expression of many different genes. In many cases due to the vector system used, applicant have noted that the resulting cells will contain only a single anti-sense expressing vector. Similar principles apply to RNAi.

When a transfected cell looses a specific phenotype, the anti-sense identity of the sense gene that has been knocked out is identified by isolating and sequencing the anti-sense expression cassette in the reserved unselected (untreated) aliquot. The anti-sense strand on the anti-sense expression cassette is the compliment of the sense gene. If the anti-sense strand in not a full length anti-sense, or does not match a sequence of a known gene, then the gene fragment can be used as a hybridization probe in order to isolate the full length gene. In essence, the anti-sense expression vector serves as a tag to identify the gene inactivation event of interest.

The method involves the selection of the pool of anti-sense expressing cells for the specific phenotype.

The goal of the selection is to separate the majority of cells which continue to maintain a specific phenotype from the rare cells in which an anti-sense inactivation event has specifically knocked-out a gene that is essential for the maintenance of the specific phenotype.

This can be based on virtually any kind of selection means. These selection means can be varied as is known to those skilled in the art. However, the following is a non-exhaustive list and is not to be construed as limiting the present invention to these listed means.

The selection means is based on the ability of the cells to:

1. Grow or survive under specific culture conditions, that is the actual selection is for the growth or survival of the cells. In an embodiment, this can be basic culture conditions, such that the selection is for growth or survival-essential genes. The selection conditions could include sub-effective doses of specific factors which at effective doses would cause growth arrest or cell killing. In this case the selection is for the identification of knock-outs which sensitize the cells to the specific added factor.

In another embodiment, the selection can be in combination with a factor that normally does not cause an arrest or killing function. In this case a knock-out could be selected which only in combination with the added factor are effective in arresting or killing cells.

In a further embodiment, the selection can be for the inability to grow or survive when a parasite or infectious agent is added to the cell of interest. In this case the selection would be for knock-outs that are targeting genes that are specifically essential for some aspect of viral or parasitic function within a cell that are only essential when that cell is infected. Since some viral infection result in the induction of survival factors (such as CrmA, p35) it is likely that at least some cell functions are different and potentially selectively needed during viral, parasite growth.

2. The second type of selection means is for the expression of a specific factor that can be measured and this measurement can be adapted for a selection. This factor can be anything that is accessible to measurement, including but not limited to, secreted molecules, cell surface molecules, soluble and insoluble molecules, binding activities, activities that induce activities on other cells or induce other organic or inorganic chemical reactions.

3. The third type of selection means is for changes in cell structure that are detected by any means that could be adapted for a selection scheme. This includes, but is not limited to, morphological changes that are measured by physical methods such as differential is sedimentation, differential light scattering, differential buoyant density, differential cell volume selected by sieving.

4. The fourth type of selection means is based on differences in gene expression that can be directly measured. This includes changes in cell surface markers, changes in biochemical activities, any changes that would be re-selected in changes in binding of fluorescent labeled probes that could be used in conjunction with a Fluorescence Activated Cell Sorter (FACS) or any property that can be used as a basis for a selection.

5. The fifth type of selection means is based on differences in gene expression that can be indirectly measured. This includes changes in transcription factor activity that are measured by a synthetic gene construct encoding a selective marker (such as a drug resistance marker or a cell surface marker that could be used in a FACS selection). This category would also include changes in mRNA stability, mRNA localization, mRNA translation control. All of these changes could be the basis of a selection because a synthetic construct which is controlled by one of these regulatory events could be constructed which would drive the expression of an easily selected gene product.

The third part of the method involves steps identifying the anti-sense knock-outs that specifically inhibit the phenotype of interest. Since the selection of the anti-sense transfected cells is based on the maintenance of the phenotype of interest, the cells of interest (those losing the phenotype) will not be present after the selection but will be present before the selection. Since the functional changes are caused by expression from anti-sense expression vectors and the inactivated genes can be identified by sequence analysis of the cloned anti-sense cDNA insert, the goal of this step is actually to identify the anti-sense expression vectors that are lost from the population of cells during the selection procedure.

The anti-sense inserts are cloned into a defined position on the vector and the sequence elements surrounding the site are known, so all the cDNA inserts can be amplified with the use of a PCR amplification using primers from the sequences that surround the insert site. Thus the goal becomes to identify DNA molecules present in one population and not in another. This is accomplished by a variety of subtraction techniques.

Some of the methods that may be used are summarized below as is known to those skilled in the art. However, the following is a non-exhaustive list and is not to be construed as limiting the present invention to these listed means. Various differential hybridization methods as well as different subtractive hybridization techniques will be used. They are summarized in some detail in the methods section.

Once fragments are identified that are lost during the selection and are candidates for genes of interest, their function must be confirmed and the gene identified in the fourth part of the method. The fragments are recloned into the anti-sense expression cassette and individually re-transfected into the target cell to determine whether the expression of the isolated fragment can really change phenotype. If the phenotype is really lost as is predicted then the isolated fragment is sequenced and used to isolate the full length sense gene.

It may also be determined whether the fragment is indeed anti-sense with the use of strand specific probes. The sense gene fragment will be used to derive antibodies that can be used to monitor expression levels to determine if there has been a functional anti-sense knock-out [Deiss et al., 1995].

The present invention is a genetic method for identifying genes that are essential for the maintenance of specific cell phenotypes. The method requires that the specific phenotype can be selected. These identified genes are excellent targets for the development of pharmacological inhibitors which would also act clinically to inhibit the specific phenotype.

Thus the present invention provides a gene discovery tool which can effectively identify pharmacological targets for inhibition of deleterious phenotypes.

The following are several examples of phenotypes but this list is not to be construed as limiting the present invention to these listed examples.

Phenotypes Related to Growth or Survival: Addressing the Problem of Unusual Growth:

This includes the problem of cancer but is not limited to cancer but is applicable to all aberrant growth events.

The method of the present invention can be used to identify genes that are essential for the growth of cells transformed under general or specific conditions.

To define genes that are essential specifically for transformed cells, an anti-sense cDNA library is introduced into transformed cells non-transformed cells of the type from which it was derived. The anti-sense constructs that interfere with transformed cell growth and not from the non-transformed cells are found by subtracting the anti-sense RNA molecules expressed in surviving cells from both transfections. Knock-outs specifically absent in the transformed cells but present in the non-transformed cells are desired. These are isolated by the methods described herein. The selection can be a most specific selection such as one where sub-lethal doses of chemotherapeutics are added during the selection. In this case the selection would include gene knock-outs that sensitize the cells to chemotherapeutic treatments.

The factors added during the selection could be ones that are thought to be present at the site of tumors.

Thus the selection includes events that sensitize cells to a localized tumor effect and could increase the specificity of anti-cancer treatment. Any growth or survival event could be used as a basis not just cancer related.

The growth or survival phenotype can also be used as a way of eliminating populations of cells that are not necessarily growing improperly but which function in a manner that is deleterious. Thus virally infected cells or parasite harboring cells could be used as a target and the un-infected or nonparasite containing cells used to subtract. This would define all the genes that are specifically essential for the cell in the presence of these insults. These would of course be excellent targets for inhibiting viral or parasite spread.

Phenotypes Related to the Release of Factors:

This class of selections includes events that increase or decrease the production of secreted factors.

These include inflammatory mediators whose release could be modulated. For example, if the production of a specific mediator is necessary for normal immune function but is produced at lethal levels in aberrant situations (such as septic shock), then one could use the production as a screen and look for events that knock-out or down-regulate productions. In a further embodiment, the selection can be done in the presence of sub-optimal doses of other drugs in order to identify sensitization events.

Phenotypes Related to Changes in Cell Functions:

These selection events are designed to identify genes that are essential for many basic cell functions that depend on any changes that can be externally selected.

Figure 2:
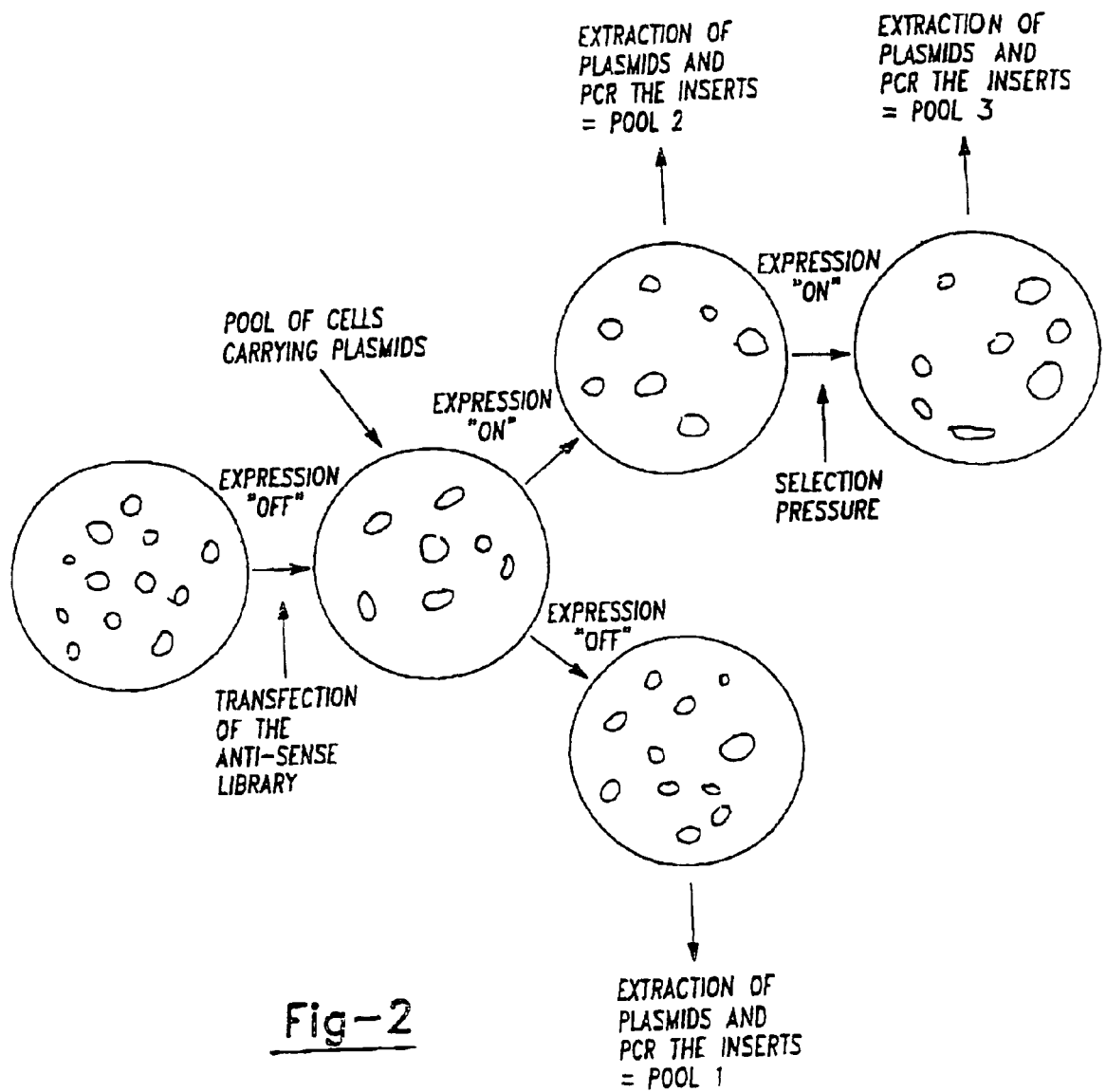
FIG. 2 is a schematic representation of the method of the present invention with a regulated anti-sense cDNA expression library.

Several permutations of the method of the present invention are possible and are presented as schematic diagrams in FIGS. 1-2. FIG. 1 provides a general outline of the gene identification method of the present invention. In this version a population of cells is first transfected with an anti-sense cDNA expression library. The expression library in this scheme codes for a drug resistance marker that is used to select transfected cells. This results in a population of cells (Population 1) that all contain anti-sense expression cassettes. The population of transfected cells is then placed under a selection pressure. Cells that survive this selection constitute population 2.

Transfected cells that become sensitive to the selection procedure will be lost or at least reduced in abundance in population 2. In order to identify the constructs that induce this sensitization the following procedure is performed. The expression cassettes contained in the two population are extracted from the cells. The cDNA inserts are excised by PCR amplification using primers that flank the cDNA cloning sites. This results in two pools of PCR fragments. To identify the elements that are lost during the selection a subtraction is done between the two pools. Elements are identified that are present in population 1 and absent or reduced in abundance in population 2.

To confirm that the subtracted fragments do indeed induce a sensitization to the selection procedure, individual fragments are recloned into the identical vector and than individually retransfected into cells.

These cells are then individually assayed for sensitivity to the selection procedure. A correctly cloned element will induce sensitization of the transfected clones to the selection procedure.

FIG. 2 provides a diagram of the method with a regulated anti-sense cDNA expression library. In this simple variation the object is to clone the anti-sense cDNA library into a vector in which expression of the anti-sense is regulatable. The method is then modified so that during the original transfection, the expression of anti-sense is turned "OFF". After cells are selected for the presence of the vector an aliquot of cells is harvested and vectors are extracted and inserts excised by PCR. This constitutes pool 1. The remaining transfected cells are treated to turn "ON" the expression of the anti-sense expression. An aliquot of these cells are taken after several cell divisions (pool 2). Again the aliquot of cells are extracted and cDNA inserts excised by PCR. Finally an aliquot of the cells with anti-sense turned "ON" is placed under a specific selection and cells after this selection are harvested.

Again following extraction and PCR amplification pool 3 is produced.

In this case we can perform two kinds of subtractions. The first subtraction is pool 2 from pool 1. This identifies anti-sense inactivations that are lethal or growth arresting. The second subtraction is subtracting pool 3 from pool 2. This identifies anti-sense knock-outs which sensitize cells to the specific selection.

Additional permutations/variations on the method of the present invention can be made. The method can be used to identify different gene expression backgrounds.

In this variation anti-sense induced sensitization in cells that express different genes is investigated. This can be accomplished by transfecting into cells that contain an inducible gene expression cassette. This cassette affords inducible expression of a specific gene construct we will call gene X for this example.

Following transfection and selection for the presence of an anti-sense cDNA library an aliquot of cells is harvested, vectors are extracted and cDNA inserts are excised by PCR. This is pool 1. The remaining cells are induced to express gene X. Allowing some time for expression, the cells are harvested, vectors extracted and cDNA inserts excised by PCR. This generates pool 2. The subtraction of pool 2 from pool 1 yields inserts that specifically sensitize cells to the expression of gene X.

In another variation the method of the present invention is used with different cell types. This variation involves transfecting two different cell types.

This could be cells of different genetic background or of different tissue origins, or even from different organisms. In the simple diagrammed case two cell types are transfected with the same anti-sense cDNA expression library. The different cell types are propagated in different containers. Transfected cells are then selected for the presence of the library. The cells containing the library are harvested, vectors extracted and cDNA inserts are excised by PCR. For each cell type a different pool is generated. The subtraction between these pools, both pool 1 from 2 and pool 2 from 1 identify anti sense knockouts that are specifically lethal or growth arresting to one cell type but not the other.

In a further variation, the method of the present invention is used for determining the fitness of specific genes in a population. In all the versions described above, populations of PCR fragments are generated which potentially differ by some number of elements due to the biological activity of those elements. The subtraction of these pools is then used as a method to identify cDNA fragments which have biological effects when expressed.

It is also possible to use the same pools to determine whether an anti-sense construct directed against a specific gene could confer some biological effect during some sort of selection. Specifically in this simple example, when two pools 1 and 2 have been generated for the operation such as in the examples, there are a variety of tools available to individually measure the relative abundance of anti sense construct representing specific cDNAs in pool 1 and pool 2. A variety of methods are known for quantitating the abundance of DNA molecules in different samples. Following is a non-exhaustive list: Southern blot analysis either using a fragment of the gene of interest as a probe against the two pools; Quantitative PCR with specific primers identifying the gene of interest; GEM analysis, using the pools 1 and 2 as the probes and hybridizing against chips of arrayed known genes.

If the abundance of the anti-sense construct significantly decreases after a selection then it is likely that anti-sense has sensitized the cells to that selection.

As shown in Example 2, sequences of genes have been identified by the method of the present invention. An anti-sense construct of these sequences delivered to a cell reduces a gene product (gene inactivation) and thereby provides sensitization of the cells to anti-Fas antibodies. These antisense constructs can be used therapeutically to sensitize the cells for antibody therapy. Antisense therapeutic construct can be delivered to the cells and can be rendered nuclease resistant as is known in the art [Agrawal, 1996; Calabretta, et al, 1996; Crooke, 1995; Felgner, 1997; Gewirtz, 1993; Hanania, et al 1995; Lefebvre-d'Hellencourt et al, 1995; Lev-Lehman et al., 1997; Loke et al, 1989; Wagner et al., 1996; Wagner, 1994; Radhakrishnan et al., 1990].

Also disclosed by the present invention is a method for the identification of genes that encode for inhibitors of cell death. This method is commonly known as the achilles heel method (AHM). This method involves introducing an antisense library into a vector such as an episomal vector (Deiss and Kimchi, 1991) enters target cells to generate a pool of cells with each cell expressing a different antisense fragment. This pool of cells will be known as Pool 1. Second, the transfactents are treated with a sub-optimal dose of an inducer and the surviving cells are collected. The surviving cells are known as Pool 2. The cells containing inactivation events that sensitize the cells to death are preferentially lost from Pool 2, and so are the antisense cDNA inserts that confer the sensitization. These cDNA inserts are recovered by subtracting the CDNA inserts containing in Pool 2 from those in Pool 1. The products of the subtraction are cloned in the episomal expression vector and individually transfected into target cells in order to confirm their ability to render the cells more sensitive to the killing inducer.

Following the subtraction of Pool 2 cDNAs from Pool 1 cDNAs, the potentially sensitizing cDNAs are cloned in an anti-sense orientation in an episomal expression vector. The anti-sense cDNA containing episomes are individually transfected into target cells in order to confirm their ability to render the cells more sensitive to the killing inducer.

Alternatively, Pool 1 and Pool 2 cDNAs are labeled and used as probes for hybridization of cDNA microarray filter. Computer analysis identifies the cDNAs depleted from Pool 2. In both cases "function profiling" is being employed to identify signal pathway inhibitors.

Recently, similar "function profiling" methods have been described for genetic analysis of *S. cerevisae* (Pat Brown and Ron Davis). These methods are well suited to yeast since they require prior knowledge of gene sequence and the ability to generate haploid cells. By contrast, AHM does not require a priori knowledge of any gene sequence or haploid cells. Thus, AHM is a powerful genetic tool for "function profiling" in mammalian cells. Moreover, AHM can be easily scaled up to generate "function profiles" of all expressed human genes.

The AHM and the TKO methods are complementary and together can be used to identify the positive and negative regulators of any pathway that can be reconstructed into human cells and culture. The AHM method identifies genes whose inactivation by antisense sensitize cells to an inducer. Thus, it enables dissection of the signalling pathway by identifying inhibitors of cell death. Since these two methods are related, the subtraction analysis is similar to that disclosed above.

There are several uses for the genes that were identified in the AHM screen for inhibitors of Fas induced apoptosis. Since the activation of the fas pathway is relevant to several different pathologies, it is useful to have modifiers of Fas induced killing. The activation of the Fas pathway is associated with detrimental effects such as liver damage in fulminant hepatitis or immune mediated tissue destruction. Conversely, proper activation of the Fas pathway is required for elimination of autoreactive T-cells and it has been shown that activation of the Fas pathway mediates some aspects of tumor suppression. Thus it would be clinically useful to be able to enhance or inhibit the Fas pathway depending on the particular situation. The identification of inhibitors of the Fas pathway can be used for both of these purposes. The inhibitors should act to sensitize cell to Fas induced killing. Thus inhibition of Nrf-2 by anti-sense inactivation sensitizes cells to killing induced by Fas. It has been shown that the inhibition of genes regulated by Nrf-2 such as Glutathione-S-transferase and NAD(P)H quinone oxireductase by Dicumarol also sensitizes cells to Fas induced killing. This shows that Dicumarol or drugs that act in a similar manner may also enhance Fas induced killing in other situations. Specifically these agents can enhance the killing of auto-reactive T-cells by Fas and thereby reduce the symptoms of auto-immunity. This can be done during the early stages of the disease since some of the ultimate tissue damage induced in auto-immunity is mediated by activation of the Fas pathway. Similarly, the enhancement of Fas induced killing can be beneficial in mediating some aspects of tumor suppression since it has been demonstrated that some tumor suppression activities are mediated through the activation of the Fas receptor. Thus the finding that Dicumarol sensitizes to Fas induced killing can be proposed to be a remedy for auto-immunity. Similarly the finding that Sulfinpyrazone also sensitizes to Fas induced cell killing also shows that Sulfinpyrazone as well as drugs that act similarly can be remedies for auto-immunity.

In this respect, the present invention provides for a method or process of treating auto-immune disease in a subject by administering to the subject a therapeutically effective amount of a compound which inhibits a gene in the Fas pathway.

Said administering step may include administering an effective amount of a compound which inhibits a gene selected from the group consisting essentially of casein kinase alpha 1, Nrf-2, basic fibroblast growth factor, TNF receptor associated factor 6, human COP9, antithrombin III, mucin 1 transmembrane, adenosine receptor A3, calcium/calmodulin-dependent protein kinase II, human protein immunoreactive with anti-parathyroid hormone antibodies and retinoic acid receptor gamma 1.

Additionally or alternatively, said administering step may include administering an effective amount of a compound selected from the group consisting essentially of dicumarol, sulfinpyrazone, Nrf2 inhibitor, CKI-7 and casein Kinase inhibitor.

Conversely, the inhibition of Fas activated killing can also have clinical benefit under certain circumstances. For example the inhibition of Fas induced killing can protect the liver from acute damage. The inhibition of the Fas pathway by over expression of the gene identified in the AHM Fas screen inhibits Fas induced cell killing. These genes are secreted molecules, thus the addition of the soluble molecule protect cells from damage. Overexpression of the inhibitors can also be achieved through a number of other means including the use of gene therapy to transduce the gene into potential target cells and protect those cells.

There are other uses of the AHM method that are directly related to the validation of AHM in identifying inhibitors of the Fas pathway. One application is to identify toxic drug interactions. Performing an AHM screen to identify genes that inhibit toxic side effects of a specific drug (drug X) is one example. It is important that the genes that are identified as inhibitors of drug X induced toxicity be fully functioning. When one of the identified genes is found to be inhibited by another drug (drug Y) then that drug Y sensitizes patients to drug X. This type of analysis permits rapid screening for drug interactions before the drugs were used on patients.

The genes identified in the Fas AHM screen are survival factors since they inhibit killing induced by Fas. As such they can be used to limit chronic or acute pathological situations in which there is excessive cell death. Such applications could include organ failure induced by heart failure, acute liver damage and ischemic stress.

Additionally, the identified targets can then be used as targets to develop inhibitors and those inhibitors can be used as cofactors to activate the identified pathway.

For example, one can identify genes, which inhibit killing induced by chemotherapeutics. Inhibition of such genes sensitizes tumors to chemotherapeutics. Such inhibitors have utility in treating cancer patients.

A list of genes were identified in the Fas AHM screen using the gene blot analysis. These genes are identified as inhibitors of Fas induced killing and are shown in the following table:

TABLE A

| Gene name | GenBank accession Number | Fold depletion from Pool 2 |
| --- | --- | --- |
| TNF receptor associated factor 6 | AA456295 | 5.25 |
| Human COP9 | AA489699 | 3.81 |
| Antithrombin III | T62060 | 3.21 |
| Mucin 1, transmembrane | AA488073 | 2.81 |
| Casein Kinase, alpha 1 | AA625758 | 2.79 |
| Adenosine receptor A3 | AA863086 | 2.47 |
| calcium/calmodulin-dependent protein kinase II | AA056626 | 2.42 |
| Human protein immunoreactive with anti-PTH antibodies | AA088258 | 2.34 |
| Retinoic acid receptor, gamma 1 | AA496438 | 2.11 |

The present invention also provides for a customized kit to practice the method of the present invention.

The kit would be assembled to include at least an expression cDNA library constructed for specified cells as they are expressing the phenotype. Further a culture of cells of the requested phenotype could also be provided in the kit.

The above discussion provides a factual basis for the method of identifying genes that are essential for the maintenance of specific cell phenotypes. The methods used are shown below and can be shown by the following non-limiting examples and accompanying figures.

Throughout this application, various publications, including United States patents and applications, are referenced by author and year and patents and applications by number. The disclosures of these publications and patents and patent applications in their entireties are hereby incorporated by reference into this application in order to more fully describe the state of the art to which this invention pertains.

EXAMPLES

General Methods

General methods in molecular biology: Standard molecular biology techniques known in the art and not specifically described were generally followed as in Sambrook et al., Molecular Cloning: A Laboratory Manual, Cold Springs Harbor Laboratory, New York (1989, 1992), and in Ausubel et al., Current Protocols in Molecular Biology, John Wiley and Sons, Baltimore, Md. (1989).

Polymerase chain reaction (PCR) was carried out generally as in PCR Protocols: A Guide To Methods And Applications, Academic Press, San Diego, Calif. (1990).

Reactions and manipulations involving other nucleic acid techniques, unless stated otherwise, were performed as generally described in Sambrook et al., 1989, Molecular Cloning: A Laboratory Manual, Cold Spring Harbor Laboratory Press, and methodology as set forth in U.S. Pat. Nos. 4,666,828; 4,683,202; 4,801,531; 5,192,659 and 5,272,057 and incorporated herein by reference.

Recombinant Protein Purification is undertaken as generally set forth in Marshak et al, "Strategies for Protein Purification and Characterization. A laboratory course manual." CSHL Press, 1996 unless otherwise specified.

Vectors are constructed containing the cDNA of the present invention by those skilled in the art and should contain all expression elements necessary to achieve the desired transcription of the sequences (see below in specific methods for a more detailed description). other beneficial characteristics can also be contained within the vectors such as mechanisms for recovery of the nucleic acids in a different form. Phagemids are a specific example of such beneficial vectors because they can be used either as plasmids or as bacteriophage vectors. Examples of other vectors include viruses such as bacteriophages, baculoviruses and retroviruses, DNA viruses, cosmids, plasmids, liposomes and other recombination vectors. The vectors can also contain elements for use in either procaryotic or eucaryotic host systems. One of ordinary skill in the art will know which host systems are compatible with a particular vector.

The vectors are introduced into cells or tissues by any one of a variety of known methods within the art (calcium phosphate transfection; electroporation; lipofection; protoplast fusion; polybrene transfection).

The host cell can be any eucaryotic and procaryotic cells, which can be transformed with the vector and which will support the production of the enzyme. Methods for transformation can be found generally described in Sambrook et al., Molecular Cloning: A Laboratory Manual, Cold Springs Harbor Laboratory, New York (1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor, Mich. (1995) and Gilboa, et al. (1986) and include, for example, stable or transient transfection, lipofection, electroporation and infection with recombinant viral vectors. In addition, see U.S. Pat. No. 4,866,042 for vectors involving the central nervous system and also U.S. Pat. Nos. 5,464,764 and 5,487,992 for positive-negative selection methods.

General methods in immunology: Standard methods in immunology known in the art and not specifically described were generally followed as in Stites et al. (eds), Basic and Clinical Immunology (8th Edition), Appleton & Lange, Norwalk, Conn. (1994) and Mishell and Shiigi (eds), Selected Methods in Cellular Immunology, W.H. Freeman and Co., New York (1980).

Immunoassays: In general, ELISAs are the preferred immunoassays employed to assess a specimen. ELISA assays are well known to those skilled in the art. Both polyclonal and monoclonal antibodies can be used in the assays. Where appropriate other immunoassays, such as radioimmunoassays (RIA) can be used as are known to those in the art. Available immunoassays are extensively described in the patent and scientific literature. See, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521 as well as Sambrook et al, Molecular Cloning: A Laboratory Manual, Cold Springs Harbor, N.Y., 1989.

Polyclonal and Monoclonal Antibody Production: Antibodies may be either monoclonal or polyclonal. Conveniently, the antibodies may be prepared against a synthetic peptide based on the sequence, or prepared recombinantly by cloning techniques or the natural gene product and/or portions thereof may be isolated and used as the immunogen. Such proteins or peptides can be used to produce antibodies by standard antibody production technology well known to those skilled in the art as described generally in Harlow and Lane, Antibodies: A Laboratory Manual, Cold Spring Harbor Laboratory, Cold Spring Harbor, N.Y., 1988 and Borrebaeck, Antibody Engineering—A Practical Guide, W.H. Freeman and Co., 1992.

For producing polyclonal antibodies a host, such as a rabbit or goat, is immunized with the protein or peptide, generally with an adjuvant and, if necessary, coupled to a carrier; antibodies to the protein are collected from the sera.

For producing monoclonal antibodies the technique involves hyperimmunization of an appropriate donor with the protein or peptide fragment, generally a mouse, and isolation of splenic antibody producing cells. These cells are fused to a cell having immortality, such as a myeloma cell, to provide a fused cell hybrid which has immortality and secretes the required antibody. The cells are then cultured, in bulk, and the monoclonal antibodies harvested from the culture media for use.

The antibody can be bound to a solid support substrate or conjugated with a detectable moiety or be both bound and conjugated as is well known in the art.

(For a general discussion of conjugation of fluorescent or enzymatic moieties see Johnstone & Thorpe, Immunochemistry in Practice, Blackwell Scientific Publications, Oxford, 1982.) The binding of antibodies to a solid support substrate is also well known in the art. (see for a general discussion Harlow & Lane Antibodies: A Laboratory Manual, Cold Spring Harbor Laboratory Publications, New York, 1988 and Borrebaeck, Antibody Engineering—A Practical Guide, W.H. Freeman and Co., 1992) The detectable moieties contemplated with the present invention can include, but are not limited to, fluorescent, metallic, enzymatic and radioactive markers such as biotin, gold, ferritin, alkaline phosphatase, 0-galactosidase, peroxidase, urease, fluorescein, rhodamine, tritium, "C and iodination.

Specific Methods

Construction of Anti-Sense Expression Vector:

This method is not limited to any specific vector system. The actual requirements are that the vector system express at high levels anti-sense molecules and that they can be identified. In a preferred embodiment the Epstein Barr Virus (EBV) Episomal vector is used [Deiss et al, 1991].

The EBV episomal vector consists of DNA segments that are necessary for the episomal maintenance of the episome both in bacteria (*E. coli*) and in human cells (this include an origin of replication and a trans-acting factor (EBNA-1). The episome also includes genes encoding resistance markers for selection either in bacteria or in human cells. Finally the vector contains a transcription cassette. Initially it will be based on the vector as described in Deiss et al. [1991], but the present invention contemplates any transcription cassette that produces high levels of anti-sense expression. The EBV episomal vector contains a RNA Polymerase II promoter and or enhancer driving the transcription of a synthetic transcript containing a set of cloning sites, a splice donor and acceptor site and a polyadenylation signal, followed by a second set of enhancers. This vector can be efficiently shuttled from animal cells to bacteria and vice versa. one procedure that allows for rapid shuttling is using the method of Hirt [1967] to extract episomal vectors from animal cells and using this preparation to transform *E. coli*. Applicants have observed that, on average, cells transfected with a library cloned into the vector contain only one expressing vector.

The specific choice of promoters and enhancers are dependent on the exact selection condition and the cell line used. This must be empirically determined for each selection condition as is known to those skilled in the art.

In an embodiment, the EBV vector can also contain an inducible expressed promoter such that the expression of the anti-sense library would be inducibly expressed by a specific inducer. This will allow additional flexibility in designing selection protocols.

Construction of Anti-Sense cDNA Library:

There are several methods available to construct directional cDNA libraries. Any of these methods would be sufficient since they result in the production of a directionally identified cDNA library and the practitioner can use the method they are most familiar with. The directional cDNA is then cloned into the expression cassette in the anti-sense orientation. A method that may be used is detailed in Deiss et al, 1991.

Briefly, it consists of making cDNA by the method of Gubler and Hoffman [1983] and making the cDNA directional by the method of Meisner et al. [1987].

The mRNA is extracted from cells that have been cultured under a variety of conditions that mimic the actual selection conditions. This is designed to ensure that the library will include all the messages that are expressed in the target cell under selection conditions.

RNA is prepared at time points that will contain messages that are always present as well as messages that are induced by the selection procedure. This is achieved by extracting RNA previous to the selection and at times during the selection. The various pools of RNA are then mixed together so that all possible RNA molecules are present [Deiss and Kimchi, 1991].

An alternative method that can be used consists of deriving a library of genomic DNA fragments cloned into the expression cassette. Since all the transcribed messages are derived from genomic DNA (with the exception of RNA edited messages; this will actually include mitochondrial DNA as well) this method would generate all possible messages. The directionality would be lost so the library would be only half anti-sense. Since the sense fragments are unlikely to frequently encode full length proteins or have biological activity the anti-sense fragments would still likely produce the most frequent biological effects. The genomic fragments are produced by restriction enzyme cleavage of genomic DNA.

It would be necessary to produce only one library per species, since with the exception of the B and T cell receptors, genomic DNA does not differ in different cell types at least in mammals (again, erythrocytes or any cells that lack nuclei are an exception).

In the case of the genomic library is be necessary to determine whether any expressed fragments express a sense or an anti-sense message. This is done by using the insert as a strand specific probe, both from the expressed and non-expressed strand in a Northern analysis. This indicates if the expressed fragment is sense or anti-sense in relation to the endogenously expressed gene.

Some sequence will match, some will not match, genes already deposited in the various databases. In the case where the identified gene matches the sequence of a gene already in a database this information would then enable the determination if the insert is a sense or anti-sense insert.

Transfection of the Anti-Sense Library:

There are a large variety of methods to transfect DNA into cell lines and cell cultures. The most efficient method for each selection is determined empirically based on experience and the known relative efficiency of each method.

The method selected must both efficiently delivery DNA into cells and not effect the biological responses that will be selected following the transfection. Viral vector system can also be used and this would entail producing infectious virus and infecting the target cells. Applicant has found electroporation to be an efficient method, but other methods can be used as are known in the art.

Identification of Differentially Expressed Antisense Messages:

The methods of identifying the differentially expressed antisense messages in a preferred embodiment includes the methods described in Braun [1996] and as described in Diatchenko et al. [1996]. These methods include a PCR amplification of subtracted populations.

Appropriate restriction sites are included in the expression vector so that following PCR amplification of the cDNA inserts, the inserts are flanked by appropriate restriction sites. Restriction digestion is then used to produce templates that are useful for these techniques.

Another method that is used is the "GEM" gene expression microarray as described in Schena et al. [1995]. In this technique, PCR fragments corresponding to a set of specific plasmids (in this case antisense cDNA inserts contained in antisense expressing vectors or other DNAs as appropriate) are fixed to a glass template and this is hybridized with two fluorescently labeled probes. In this specific case, the probes are reverse transcribed antisense transcripts derived from cells transfected with the antisense expression library either before or following a selection.

Generation of Efficient Antisense Inhibitor:

In addition to assaying expression cassettes where all the transcripts are directionally cloned in the antisense orientation, another strategy employed in the present invention is to generate randomly primed cDNA and cleave the cDNA with two restriction enzymes (hereby represented by "X" and "Y") and clone the resulting mixture into two different expression cassette. In the first cassette site, X would transcriptionally precede Y, and the second cassette site, Y would transcriptionally precede X. In this arrangement, the cDNA is divided into sections that may have different abilities to serve as an efficient antisense inhibitor. The strongest differential signal is likely to be produced by the fragment that is the most efficient antisense inhibitor. Thus, the screening is more likely to produce a meaningful differential signal.

Specific Examples

Example 1

Determination of Combination of Methods for Preferred Embodiment

The method requires two distinct major steps as described herein above. It is greatly advantageous if this method can be applied to a wide variety of cells and situations. In the first step genes are inactivated in order to determine whether individual genes are essential for a specific phenotypic change. It is advantageous if these inactivation will have a phenotype both in haploid cells and in diploid cells. Since many cells of interest are diploid in nature. Furthermore, it is also an advantage if the inactivation method allows for the rapid identification of the inactivated genes. This can be achieved in a variety of manners. The inactivation methods are generally based on one of three different principles.

The first principle is that genes can be functionally inactivated by expressing mRNA that is derived from the anti-sense strand of the sense message.

This allows for inactivating the mRNA in the cell and does not require a specific gene dose. This can work for single copy or multiple copy genes either from haploid or diploid organism. It has been shown that anti-sense inactivation can be effective in a wide range of organisms including bacterial, plant and animal.

Applicants and others have extended the original observation by generating anti-sense expressing cDNA libraries. Applicants termed this method Technical Knock Out (TKO). These libraries contain collections of many (usually 100,000 to 1,000,000) different anti-sense expression constructs that will individually express a single anti-sense RNA molecule when transfected into appropriate target cells. Since these libraries contain large collections of these vectors they in effect can express anti-sense RNA to virtually all expressed mRNA molecules. Several investigators have used these type of libraries to inactivate genes and change the phenotype of cells. Once an altered cell is identified the expression cassette contained in the cells can be identified since the expression cassette DNA sequence is known. Subsequently, the anti-sense expressed cDNA molecule that is contained in the expression cassette is identified. This can be achieved by a variety of methods; applicants have used two methods. The first method involves shuttling the vector from animal cells into bacterial cells. Once the vector is in bacterial cells it is easy to produce large amounts of the vector for further analysis. The second method we have employed involves PCR amplification of the cDNA inserts by designing PCR primers that flank the cDNA cloning site on the vector. The flanking vector sequences are known so it is easy to chose appropriate primers. PCR amplification with these primers amplifies any cDNA molecules that were present between the two primers. The anti-sense approach also allows for tagging of the inactivation event. That is the identity of the sense message generally can be determined by sequencing the anti sense construct. This construct can then be identified and isolated from the phenotypically altered cells.

The second gene inactivation method that fits these requirement is an inactivation method that relies on production of "dominant negative" fragments of genes from an expression cDNA library. This method is called the Genetic Suppressor Element method (GSE). It is based on the observation that small fragments of a gene when expressed may interfere with the normal function of the full length gene product and in fact interfere with the normal function. In this manner these gene fragments were called "dominant negatives". A GSE library thus consists of fragmented cDNA molecules which are cloned into an expression cassette. When expressed from translation initiation signals in the cDNA molecule, or from translation initiation signals present in the expression cassette, these gene fragments can interfere with gene function. In addition the libraries used in the GSE method also include some anti-sense fragments and therefore gene inactivation can occur either by anti-sense or by dominant negative inactivation of gene function.

The third method of gene inactivation that could be used is called "Random Homozygous Knock-Out" (RHKO). In this method gene inactivation is achieved in two steps.

A retroviral vector is used to infect target cells. The integration of the retroviral element itself can lead to inactivation of one copy of a gene if the integration event itself functionally disrupts the normal transcription or activity of the gene in which it integrates. The retroviral vector used has an additional property that it encodes a transcription element that should transcribe into the chromosomal location in which it has integrated. In the case that this generates and anti-sense RNA transcript, additional copies of the gene could be inactivated. Thus this method also relies on anti-sense inactivation.

The TKO method was chosen for generating inactivations in these examples as the preferred embodiment because the other methods described above are not as compatible with the second step in the method of the present invention as the TKO procedure. However, as improvements become available in these methods they could be used.

In the GSE method both sense and anti-sense gene fragments are generated which are expected to have different biological activities. It is difficult to distinguish closely related gene fragments of this sort by the methods that will be used in the second part of the gene identification method of the present invention.

Thus the rare molecules that cause biological changes when expressed would be very difficult to distinguish from many similar molecules that would not have biological effects. The molecules that do not have effects would in essence mask the active molecules.

The RHKO method was also difficult to adapt to a high throughput subtractive procedure. The potential anti-sense fragments generated in this procedure must be cloned out individually and this is a process that is hard to adapt to subtraction.

The TKO method was easily adapted to subtraction.

The cDNA inserts contained in expression vectors should be all or at least mostly anti-sense in nature. The cloning procedure outlined in Deiss and Kimchi was used.

This generates anti-sense cDNA libraries and results in libraries that are biased to be anti-sense. It is possible to obtain some sense cDNA inserts with this method. Thus since most of the fragments are antisense the subtraction step will be mainly between different cDNA fragments that were expressed as anti-sense constructs. Again the principle of the present invention is that the abundance of an anti-sense construct(s) that induces a disadvantageous phenotype will be reduced after a biological selection. In order to identify these constructs, the TKO method was chosen for the gene inactivation step of the present invention.

It can be used in a variety of cell populations, both in haploid, diploid and aneuploid cells. It can be easily scaled up to involve 100,000 events or more without undue expense, and it can be easily adapted to the subtractive methods that are needed in the second part of the method of the present invention.

The second step in the gene identification method requires identification of the loss of specific anti-sense gene constructs from a large population of anti-sense constructs that are not lost. This can be accomplished in a variety of different ways. Because it is a great advantage to be able to identify specific losses in the presence of large numbers of molecules that are not lost we needed a method that has a high throughput capacity. One method that fits this requirement involves using high density arrayed chips such as the GEM chips. These are arrayed dots containing specific DNA molecules corresponding to genes. The dots are arrayed at high density on a glass coverslip with the position of each dot and the identity of the DNA molecule fixed on each dot precisely determined. Two probes derived from different population of DNA or RNA molecules are labeled with two different fluorescent dyes and hybridized to the arrays. After appropriate washing the relative binding of the dyes at each dot is determined.

The amount of dye bound at each spot reflects the abundance of the gene fixed on that dot relative in the whole population. Thus when two populations of DNA molecules are labeled with different dyes one can accurately determine whether there has been a change in relative abundance of individual molecules in the population. If there is no change the ratio of the two dyes will be one. If there has been a change in abundance then the ratio of the two different dyes will also change. This method can rapidly measure the changes of large numbers of genes in a large population. A copy of the DNA fix on each dot is stored and can be retrieved for further analysis. Although in the following example the GEM method was not used to measure the loess of anti-sense constructs it is a method that can be used in the practice of the present invention.

A second method used to identify the loss of specific anti-sense gene constructs from a large population of anti-sense constructs that are not lost is called "Subtraction". This involves manipulating two populations of DNA or RNA molecules so that only molecules that are present in one population and not in another are recovered. The version that was actually used is called PCR-Select which is a commercially available kit from CLONTECH. Briefly 1. Two populations of double stranded DNA are generated. It is assumed that some of the dsDNA molecules are present in only one of the populations (or at least much more abundant in one population).

2. These populations are separately processed. The population that is assumed to have extra species of molecules is called the tester sample. The second population that is assumed not to have these specific species is called the driver. The tester population is separately ligated to two different linkers. This generates tester population 1 and tester population 2.

The driver is left without linkers.

3. A series of manipulations including denaturation and renaturation of the driver and tester in various combinations is used. This results in generating a series of DNA molecules that have different set of linkers at their ends. The only product that can be effectively PCR amplified at the end of the manipulations are those that are present in the tester and absent (or reduced) in the driver. These molecules are easily isolated after the last PCR step.

The net result of this method is that a population of gene fragments that are present in one population and lost or absent in another population is rapidly isolated.

This is exactly what is needed in the gene identification method. These PCR products can be isolated by standard techniques and be used for further analysis as shown in Example 2.

Example 2

Identification of Genes in HeLa Cells that are Involved in fas Antibody Sensitivity The method of the present invention was applied to HeLa cells treated with anti-Fas antibody in order to identify genes that when knocked-out cause sensitization of HeLa cells to the action of anti-Fas antibodies.

HeLa cells are derived from a human cervical carcinoma and were used in the original TKO [Deiss and Kimchi, 1991]. HeLa cells were used as an exemplar of the method of the present system as they are easily grown in culture, are easily transfected and respond to anti-Fas antibody treatment.

Anti-Fas antibody (Kamiya Biomedical Company, Seattle, Wash., catalog number: MC-060) is directed against Fas/CD95/Apo-1, a transmembrane receptor that is known to signal a death response in a variety of cell types. This antibody is an activating antibody, that is, the binding of the antibody mimics the effects of binding of ligand. Applying the appropriate dose to responding cells has been shown to lead to induction of cells death (Deiss et al., 1996). HeLa cells respond to this treatment.

In this exemplar genes are identified that regulate the sensitivity of HeLa cells to killing by anti-Fas antibody. Specifically, genes are identified whose loss sensitizes HeLa cells to anti-Fas treatment.

The outline of the procedure is as follows:

1. HeLa cells were transfected with an anti-sense cDNA library.

2. Cells containing anti-sense expression vectors were isolated by selection with Hygromycin. Since the vector contains the Hygromycin resistance marker, the selection of the transfected cultures with Hygromycin generated a population of cells which contain the anti-sense expression cassettes.

3. Aliquots of this pool of cells were treated with anti-Fas antibody under two different experimental conditions. It should be noted that more conditions could be screened at the same time.

a. Treatment with a sub-lethal dose of anti-Fas antibody (10 ng/ml). Cells that are super-sensitive to treatment with anti-Fas antibody were killed whereas the majority of the population which is resistant to the treatment proliferated.

b. In the second condition, the cells were treated with a lethal dose of anti-Fas antibody (100 ng/ml). The cells were harvested at 24 hours, before the majority of cells had been killed. In this case, applicants were looking for anti-sense events that accelerate the killing associated with anti-Fas treatment as another type of sensitization.

4. Aliquots of the cells just before the treatment with anti-Fas antibody and just after the treatment with anti-Fas antibody were harvested. The DNA contained in each cell population was extracted.

5. The anti-sense cDNA inserts contained in these DNA samples were preferentially amplified through the use of PCR (see details below).

6. The pools of anti-sense cDNA fragments that were derived from cells after treatment were subtracted from those before treatment (see details below). This generated a set of cDNA fragments that were present in cells before treatment but were absent after treatment.

These fragments are good candidates for sensitizing cDNA fragments. In other words, it is likely that expression of some of these fragments leads to the inactivation of genes which causes cells to become super-sensitive to anti-Fas antibody treatment. These super-sensitive cells are quickly killed at a lower dose of anti-Fas antibody or more rapidly than the majority of cells. These cells are therefore lost from the treated cultures but are present in the untreated population. Likewise, the plasmids inducing this super-sensitivity are present in the cells before treatment but are absent from the cell sample taken after treatment. Thus, these fragments are identified during the subtraction.

7. The cDNA fragments generated by the subtraction were cloned into the original expression vector.

Appropriate restriction enzyme sites were generated or maintained during the subtraction procedure so that the recloned construct is exactly identical to the construct in the originally transfected cells. The sequence of the isolated cDNA fragments was determined.

8. The anti-sense expression plasmids containing the cDNA inserts that were identified in the method of the present invention were individually re-transfected into HeLa cells and the transfectant cells were assayed for sensitivity to anti-Fas antibody treatment.

Specific Materials and Methods

HeLa cells were transfected with anti-sense cDNA library cloned in the episomal vector, anti-sense expression vector pTKO-1. This is the same library described in Deiss and Kimchi [1991]. One million cells plated in a 100 mm dish were transfected with 15 µg of DNA containing the anti-sense cDNA library, by using the Superfect reagent (Qiagen, Santa Clarita, Calif.) as suggested by the manufacturer. Two days following transfection, cells were treated with Hygromycin B (200 [µg/ml) (Calbiochem-Novabiochem Corporation, La Jolla, Calif.). Following two weeks of selection, the population of cells was completely resistant to Hygromycin B.

These cells were plated in triplicate at a density of $2.5 \times 10^6$ cells per 150 mm dish in the absence of Hygromycin B. One plate was treated with anti-Fas antibody at 10 ng/ml (clone CHI-11 Kamiya Biomedical Company, Seattle, Wash.) for five days, the second plate was treated with 100 ng/ml of anti-as antibody for 24 hours and the third plate was UN-treated for 24 hours.

Following the treatments, the cells were harvested by washing twice with ice cold PBS (NaCl 8 g/liter; KCl 0.2 g/liter; $Na_2HPO_4$ 1.44 g/liter; $KH_2PO_4$ 0.24 g/liter; final pH of solution adjusted to pH 7.4 with HCl) and concentrated by centrifugation (15,000×g for 15 seconds). DNA was extracted by using solutions P1, P2 and P3 from the Qiagen Plasmid Purification Kit (Qiagen, Santa Clarita, Calif.). The cell pellet was resuspended in 200 µl of solution P1 (50 mM Tris-HCl, pH 8.0; 10 mM EDTA; 100 µg/ml RNase A) then mixed with 200 µl of solution P2 (200 mM NaOH, 1% SDS) and incubated five minutes at room temperature. 200 µl of solution P3 (3.OM Potassium Acetate, pH 5.0) were added and incubated two minutes at room temperature, followed by a ten minute centrifugation at 15,000×g. The clear supernatant was mixed with an equal volume of isopropanol and centrifuged at 15,000×g for ten minutes. The precipitated DNA was resuspended in 100 µl of water and stored frozen until use.

For PCT amplification of the cDNA inserts contained in these DNA preparations, the following reaction was set in a total volume of 100 µl: 1 µl of the DNA, 200 µM of dATP, dGTP, dCTP, dTTP, 500 ng each of primers; 10 mM Tris-HCl pH 9.0; 0.1% Triton X-100; 1.0 mM MgCl and 1 unit of Taq DNA polymerase (Gibco/BRL, Gaithersburg, Md.). This reaction was incubated in a Thermocycler 2400 (Perkin-Elmer, Foster City, Calif.) according to the following protocol: First, the reaction was heated to 94° C. for five minutes, then was cycled 25 times using the following three temperatures: 58° C. for one minute, 72° C. for five minutes, 94° C. for one minute. After 25 cycles, the reaction was incubated at 72° C. for seven minutes.

This resulted in amplification of the cDNA inserts. Primers were designed such that the end of the cDNA insert that is proximal to the promoter in the pTKO-1 vector is exactly flanked by a HindIII restriction site (this site is present in the vector) and the end of the cDNA that is distal to the promoter in pTKO-1 vector contains a BamHI restriction site. The BamHI site was created by altering a single base in the sequence immediately adjacent to the distal cDNA insert site, by PCR. When the library was generated [Deiss and Kimchi, 1991], this site distal to the promoter was generated by the fusion of a BamHI restriction site (derived from the cDNA fragments) and a BglII site (derived from the vector). This fused site is resistant to cleavage by either enzymes, but a single base change restored the cleavage by BamHI. Thus, the amplified cDNA fragments are flanked by a HindIII restriction site on the promoter proximal side of the cDNA and by a BamHI site on the promoter distal side.

This allowed the exact re-cloning of the fragments into the pTKO-1 expression vector with exact conservation of sequence and orientation.

Following the PCR reaction, the mixture was cleaved with BamHI and HindIII (Gibco/BRL, Gaithersburg, Md.) as described by the manufacturer. The digestion products were purified using the Wizard PCR Prep Kit (Promega, Madison, Wis.). This generated cDNA inserts with HindIII and BamHI ends.

These nucleic acid fragments were subjected to subtraction using the PCR-Select Kit (Clontech, Palo Alto, Calif.) according to the instructions of the manufacturer with the following modifications. The driver was the PCR products derived from the untreated samples and two testers were used. The first tester was derived from cells treated with 10 ng/ml anti-Fas antibody and the second tester was derived from cells treated with 100 ng/ml of anti-Fas antibody. First modification: the subtraction was done between dsDNA pools so no cDNA synthesis is required. The fragments generated from the previous step were used directly in the subtraction. Thus, applicants began at Step IV F3 in the instructions (preparation of the adapter ligated tester cDNA). The second modification was the replacement of the blunt end ligation of adapter 1 and adapter 2R with cohesive end adapters. These cohesive end adapters were ligated to the BamHI and HindIII cleaved PCR fragments generated in the step above. The cohesive ligation is usually more efficient than blunt end ligation and since applicants use cDNA flanked by different restriction sites allowing the orientation of the fragments to be maintained when recloning the subtracted products. If the blunt end ligation is used, it would not allow distinguishing one end from the other and applicants would not be able to determine the relative orientation of the cDNA in the original expression cassette. Thus, adapter 1 was replaced by an equal mixture of the appropriate primers. The same applies for adapter 2R. The other primers were of identical sequence as described in the kit. The manual supplied by the manufacturer with the kit was followed from the point of ligation of the adapters to the tester (Section IV F3 in the Manual). 0.3 µg of the tester was taken for adapter ligation. The initial hybridization included 0.9 µg of the driver and 0.03 µg of the adapted ligated tester. At the conclusion of the subtraction, a final PCR reaction is done using nested PCR primer 1 and nested PCR primer 2R. This material contains the cDNA fragments that were present in the untreated sample but absent from the treated samples. The product of this PCR reaction were re-cloned into the anti-sense expression vector.

Re-cloning of the subtracted fragments was accomplished by cleaving the subtracted population with BamHI and HindIII and purifying the cleaved products with the Wizard PCR Prep Kit (Promega Madison, Wis.).

The cleaved products were then directly cloned into the pTKO1-DHFR vector between the HindIII and BglII sites.

This replaced the DHFR sequences with the cDNA. This is precisely the procedure that was used to generate the anti-sense cDNA expression library. Thus, the fragments that were generated by the subtraction were exactly re-cloned into the original anti-sense expression vector that was used to transfect cells at the beginning of the procedure. The re-cloned constructs exactly duplicate the constructs that were present in the library. The re-cloned constructs were introduced into bacteria and DNA was extracted from the bacteria following conventional methods. These DNA preparations were used as a template for sequencing in order to determine the nucleotide sequence of the isolated cDNA inserts.

In addition, plasmids carrying the re-cloned inserts were transfected into HeLa cells to confirm their ability to induced super-sensitization to anti-Fas antibody treatment in HeLa cells.

HeLa cells were transfected with 15 µg of plasmids or control vectors as described for transfection of the original library. The cells were selected for two weeks for resistance to Hygromycin B treatment (200 µg/ml).

This selects for cells which contain expression cassettes. One million cells were plated in a 100 mm dish and treated with anti-Fas antibody. Effects of anti-Fas antibody on the transfected cultures were quantified by MTT assays as described by the manufacturer (Sigma, St. Louis, Mo.)

Analysis of the Isolated DNA Sequences

The clones were sequenced using a primer which anneals close to the edge of the cDNA which is distal to the promoter in the antisense expression cassette. Thus, in the case that the sequence matches the sense strand of a known gene then the insert is in the antisense orientation. Sequences were compared to the combined nonredundant database and the dbest compiled at the NCB1 using the Blastn program with default parameters. New and known sequences were determined by the method of the present invention, some of which are detailed in Table A; see also genes discussed in Example 3.

As described above, the isolated fragments were recloned and then reassayed for sensitivity to treatment with anti-Fas antibody (50 ng/ml for 72 hrs) using the MTT assay. These assays showed that expression of two of the fragments resulted respectively in a 1.6 and 2.0 fold increase in sensitivity to anti-Fas antibody treatment whereas expression of CrmA (a protective protein) resulted in a 2.3 fold reduction in sensitivity. This demonstrates that the method of the present invention can be successfully used to identify genes based on a positively selected phenotype.

For further information on the methods of the present invention and the fragments and genes isolated thereby, see co-assigned PCT publication No. WO 98/21366, co-assigned U.S. Pat. No. 6,057,111, and co-assigned PCT publication No. WO 01/57189 which are hereby incorporated by reference in their entirety.

Example 3

Figure 3:
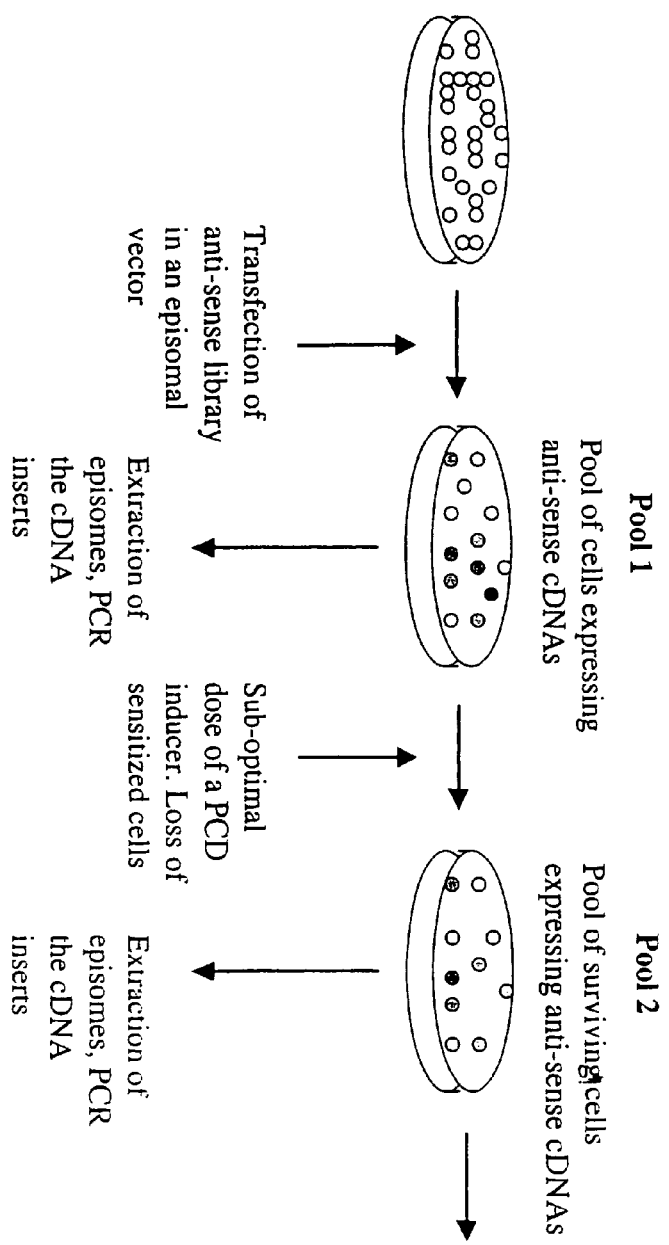
FIG. 3 is a schematic representation of the AHM method of the present invention.

The Achilles Heel Method utilizes functional profiling as diagrammed in FIG. 3. The first step consists of introducing an anti-sense expression library (Deiss and Kimchi, 1991) into target cells to generate a pool of cells, each expressing a different anti-sense fragment (Pool 1). Then, the transfectants are treated with a sub-optimal dose of a PCD inducer and the surviving cells are collected (Pool 2). Cells containing inactivation events that sensitize the cells to killing are preferentially lost from Pool 2. Consequently, the anti-sense cDNAs contained in the sensitized cells are depleted from Pool 2. The "sensitizing" cDNA inserts that are present in Pool 1 but depleted from Pool 2 are identified by two methods, subtraction or hybridization to cDNA microarray. Following the subtraction of Pool 2 cDNAs from Pool 1 cDNAs, the potentially sensitizing cDNAs are cloned in an anti-sense orientation in an episomal expression vector. The anti-sense cDNA containing episomes are individually transfected into target cells in order to confirm their ability to render the cells more sensitive to the killing inducer. Alternatively, Pool 1 and Pool 2 cDNAs are labeled and used as probes for hybridization of cDNA microarray filter. Computer analysis identifies the cDNAs depleted from Pool 2. In both cases "function profiling" is being employed to identify signal pathway inhibitors. Recently, similar "function profiling" methods have been described for genetic analysis of S. cerevisae (Pat Brown and Ron Davis). These methods are well suited to yeast since they require prior knowledge of gene sequence and the ability to generate haploid cells. By contrast, AHM does not require a priori knowledge of any gene sequence or haploid cells. Thus, AHM is a powerful genetic tool for "function profiling" in mammalian cells. Moreover, AHM can be easily scaled up to generate "function profiles" of all expressed human genes.

AHM is used to identify inhibitors of the Fas induced PCD pathway. Fas is a trans-membrane death receptor of the TNF super family. The binding of Fas ligand to Fas results in the cascade of events that lead in most cell types to apoptosis. Fas induced killing is utilized in different physiological processes as follows: (for review see Nagata, Gloldstein etc): elimination of auto-reactive T-cells, tumor induced immune suppression and destruction of virally infected cells, transformed cells and b-cells in cases of Insulin Dependent Diabetes Melitus (IDDM). In addition, activation of the Fas pathway has been suggested to play a role in liver damage, brain damage, arteriosclerosis and tumor suppression. Modulation of the Fas pathway has clinical implications in animal models: inhibition of Fas induced PCD by caspase inhibitors limits liver damage in mice and acceleration of Fas induced killing ameliorate the auto-immune phenotype of gld mice. Thus, identifying regulators of the Fas pathway that can be used as targets for drug development will have great clinical impact.

For the identification of inhibitors of Fas induced cell death, AHM was applied to HeLa cells that were treated with sub-lethal dose of Fas agonistic antibody. The latter mimics the binding of Fas ligand to Fas and induces apoptosis. "Function profiling" was performed to identify "sensitizing" cDNA fragments by using subtraction and gene array analysis. cDNA inserts from Pool 2 were subtracted from Pool 1 cDNAs and the recovered cDNAs were further analyzed. Sequencing of 226 fragments revealed 168 unique sequences, of which 53% are novel and 47% correspond to known genes. Six out of seven randomly chosen cDNAs that were individually transfected into HeLa cells conferred increased sensitivity to Fas induced killing cells, ranging between 2.9 to 5.3 fold. These fragments include three novel sequences and three fragments of previously described genes. One of the cDNA inserts is an anti-sense fragment of human Basic Fibroblast Growth Factor (FGF-2, bFGF) and the other is an anti-sense fragment of the cap-n-collar b-zip transcription factor NF-E2 related factor 2 (NRF2).

bFGF is a potent survival factor that plays a role in development, angiogenisis and in cell migration. Previous reports show that down regulation of bFGF by anti-sense expression or by blocking antibodies result in loss of a transform phenotype, reduced tumor growth and reduced angiogenesis. Five different polypeptides of 34 kD, 24 kD, 22.5 kD, 22 kD and 18 kD are translated from the human bFGF gene, initiating at different sites and terminating at the same position. The anti-sense cDNA fragment isolated in the subtraction is 295 nucleotides long and corresponds to nucleotide 890 to 1184 of the bFGF gene. It spans the last 60 nucleotides of the coding region (shared by all bFGF polypeptides) and a portion of the 3' untranslated region.

Figure 4A:
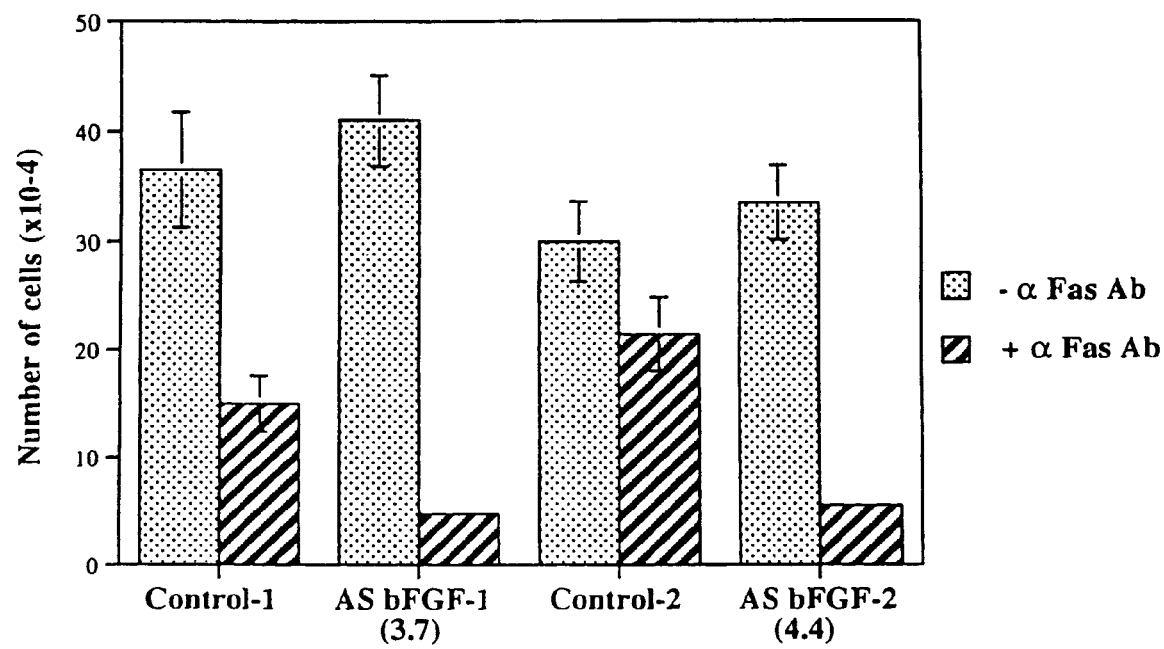
FIGS. 4A-C show the effect of the AHM method on cell proliferation; A. shows how anti-sense bFGF sensitizes HeLa cells to Fas induced PCD; B. shows the levels of expression of bFGF; C. shows the quantitation of the levels bFGF forms.

In order to confirm that anti-sense bFGF confers sensitivity to Fas, pools of cells transfected with control vector (harboring no insert) or with anti-sense bFGF were generated and treated with sub-optimal dose of anti-Fas antibody. Analysis of two independent pools of transfectants demonstrates that under conditions that results in 59% and 29% killing of the vector transfected cells, anti-sense bFGF transfected cells are 3.7 and 4.4 fold more sensitive to killing (FIG. 4A). This significant increase sensitivity of anti-sense bFGF transfected cells was reproducible in six independent pools of transfectants. It is not due to altered growth rate of the anti-sense bFGF transfected cells (compare the number of untreated cells in the control vector transfected pools to the number of untreated cells in the anti-sense bFGF transfected pools) or to a non-specific increase in sensitivity of anti-sense transfected cells to Fas induced killing since anti-sense cDNAs were previously isolated that render transfected cells resistant to Fas induced apoptosis. Complementary to the bioassay experiments, quantitative Southern analysis of Pool 1 and Pool 2 indicates that the abundance of anti-sense bFGF cDNA is reduced by 1.9 fold in Pool 2 of cells surviving sub-lethal dose of anti-Fas antibody, compared to Pool 1.

Figure 4B:
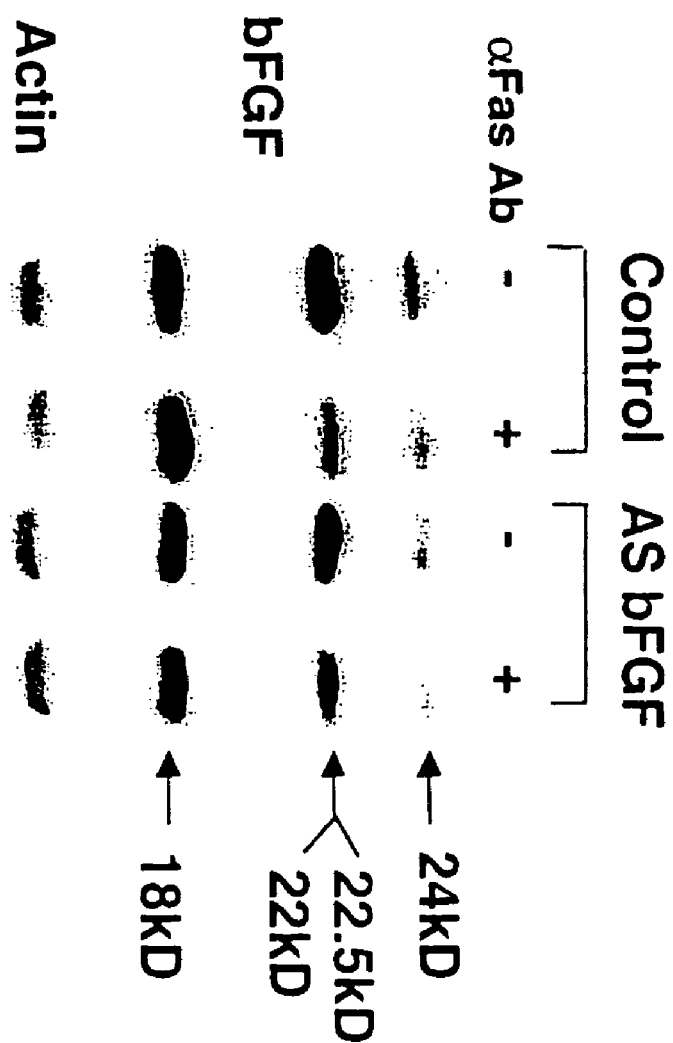
Figure 4C:
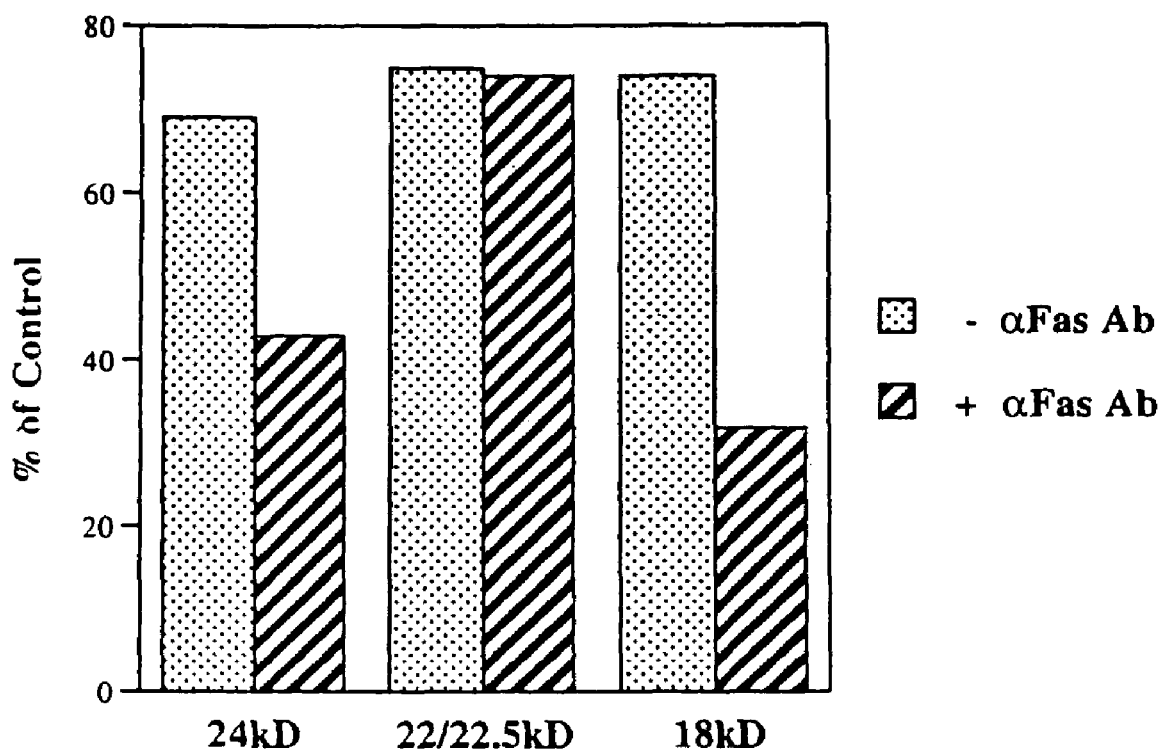

Western blot analysis of control vector transfected cells as well as anti-sense bFGF transfected cells revealed four polypeptides of 24 kD, 22/22.5 kD and 18 kD, while the 34 kD form is not detected by the antibody used (FIG. 4B). Quantitative analysis of the relative level of bFGF forms revealed that in the absence of anti-Fas antibody, expression of anti-sense bFGF results in reduction of approximately 25%-30% in the levels of each of the detected forms (FIG. 4C). Interestingly, in cells treated with anti-Fas antibody a more significant reduction in the levels the 24 kD form and 18 kD is observed, 57% and 66% respectively, while the reduction of the levels of the 22/22.5 kD is not altered. Selective reduction in the level of some of the bFGF forms by an anti-sense fragment that overlaps the coding region of all the bFGF polypeptides can be due to a network of feedback regulation loops as previously reported for some bFGF forms.

While previous studies has shown that over-expression of the 34 kD form protects cells from serum deprivation induced killing and over-expression of the 24 kD form protects cells from ionizing radiation, here it is demonstrated that bFGF is an inhibitor of Fas induced apoptosis, as identified by AHM.

The second inhibitor of the Fas pathway that was identified by AHM is the cap-n-collar b-zip transcription factor NF-E2 related factor 2 (NRF2). Nrf2 activates the transcription of phase II detoxifying enzymes such as NAD(P)H quinone oxireductase (NQO1) and Glutathione S-transferase (GST) by direct binding to the Antioxidant Response Element (ARE) in the promoter of these genes. Studies of nNrf2 null mice indicate that Nrf2 is essential for the transcriptional activation of phase II enzymes. NQO1 and GST act in concert with phase I detoxifying enzymes (such as cytochrome p-450 monooxygenase) to mediate the cellular detoxification of xenobiotics. In the absence of Nrf2, this coordinated detoxification is impaired and toxic products from phase I reactions can accumulate. In the AHM screen an anti-sense fragment of Nrf2 corresponding to nucleotide 147 to 970 of the human Nrf2 (gbS74017, Moi et al, 1994, PNAS 21, 9926) was recovered.

Figure 5A:
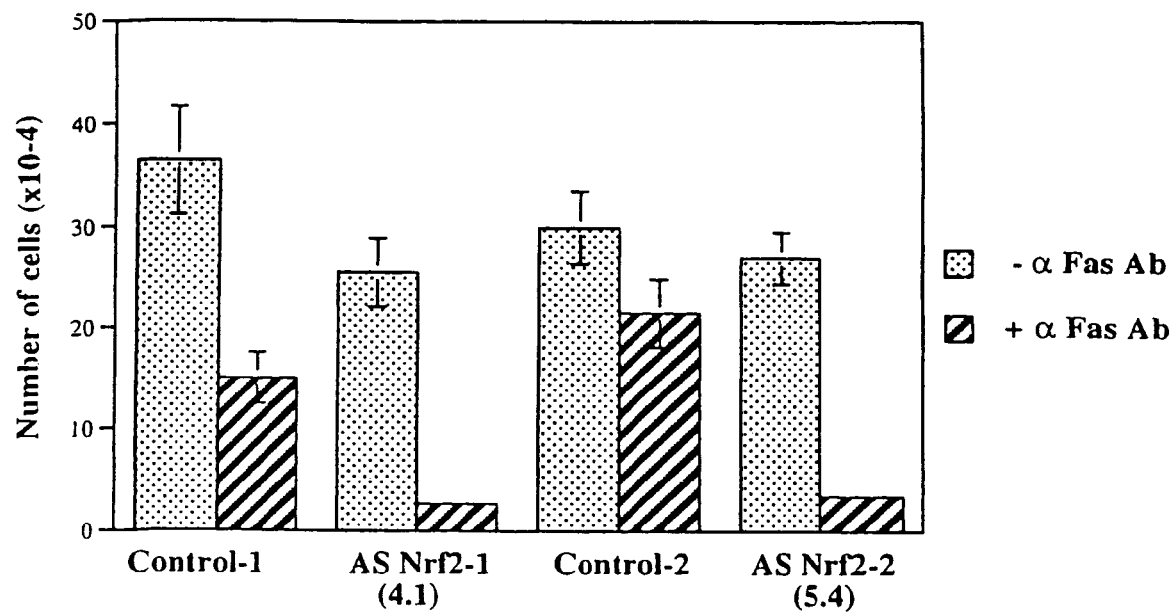
Figure 5B:
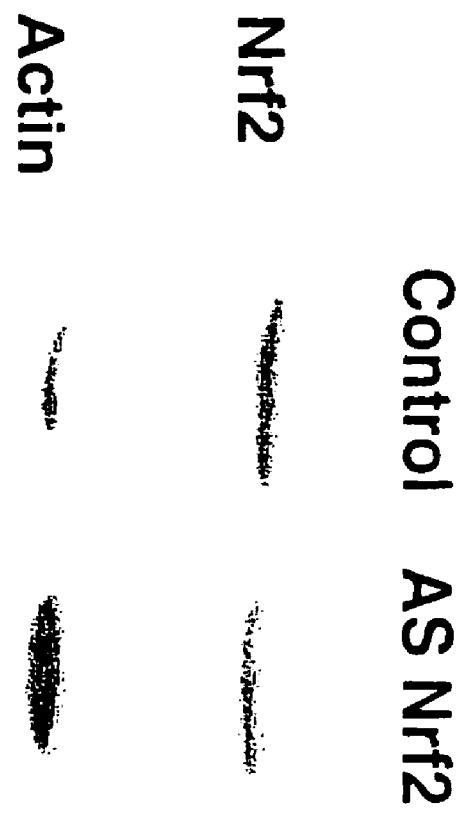

Bioassays of two pools of HeLa cells transfected with anti-sense Nrf2 clearly demonstrates that anti-sense Nrf2 render the cells 4.1 and 5.4 fold more sensitive to Fas induced apoptosis (FIG. 5A). Again, this increased sensitivity is not a result of impaired growth, since there is only limited alteration in the growth rate of anti-sense Nrf2 transfected cells (FIG. 5A). Sensitization by anti-sense Nrf2 was reproducible in seven independent pools of transfectants. Western blot analysis indicated a significant 3.8 fold reduction in the level of Nrf2 protein in the anti-sense Nrf2 transfected cells (FIG. 5B).

Figure 5C:
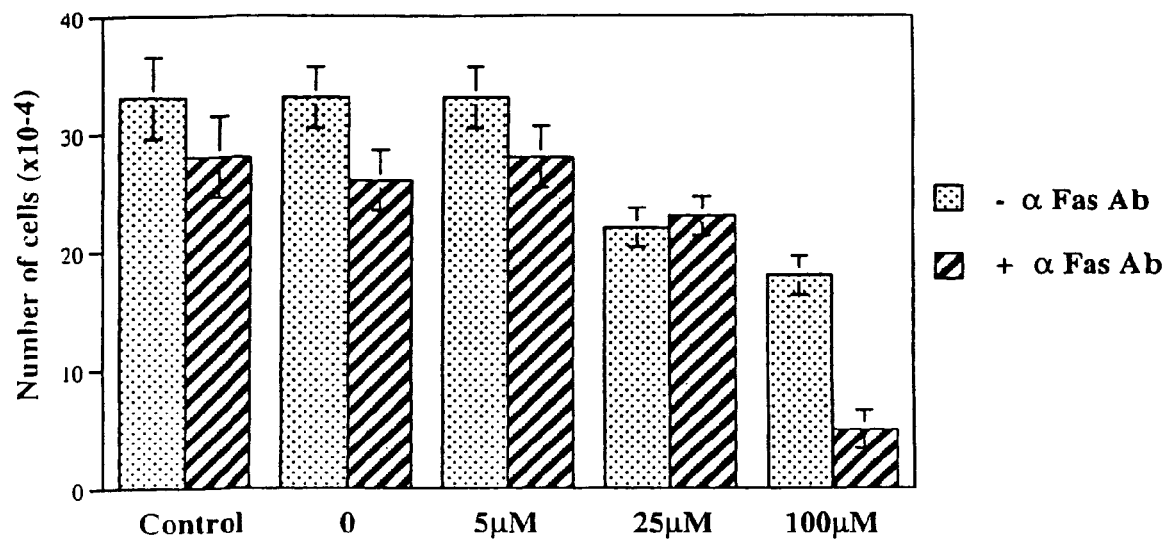

The role of Nrf2 as an inhibitor of the Fas pathway was further validated by pharmacological agents. It is predicted that treatment of cells with Dicumarol, an inhibitor of GST and NQO1 will sensitize cells to Fas induced apoptosis, since Nrf2 up-regulates the levels of GST and NQO1. As shown in FIG. 5C, HeLa cells treated with 100 mM Dicumarol are 2.8 fold more sensitive to Fas induced killing compared to cells treated with vehicle (fold sensitization was calculated as described in FIG. 4A).

Since down regulation of Nrf2 sensitizes cell to Fas induced apoptosis, it was questioned whether increasing any of the activities induced by Nrf2 will protect HeLa cells from apoptosis. Nrf2 up-regulates GST that conjugates glutathione to the reactive products of phase I detoxification. Increased activity of GST will protect cells from Fas induced apoptosis. GST activity was elevated by treating HeLa cells with the glutathione precursor N-acetyl Cysteine (NAC) that increases the glutathione pool.

Figure 5D:
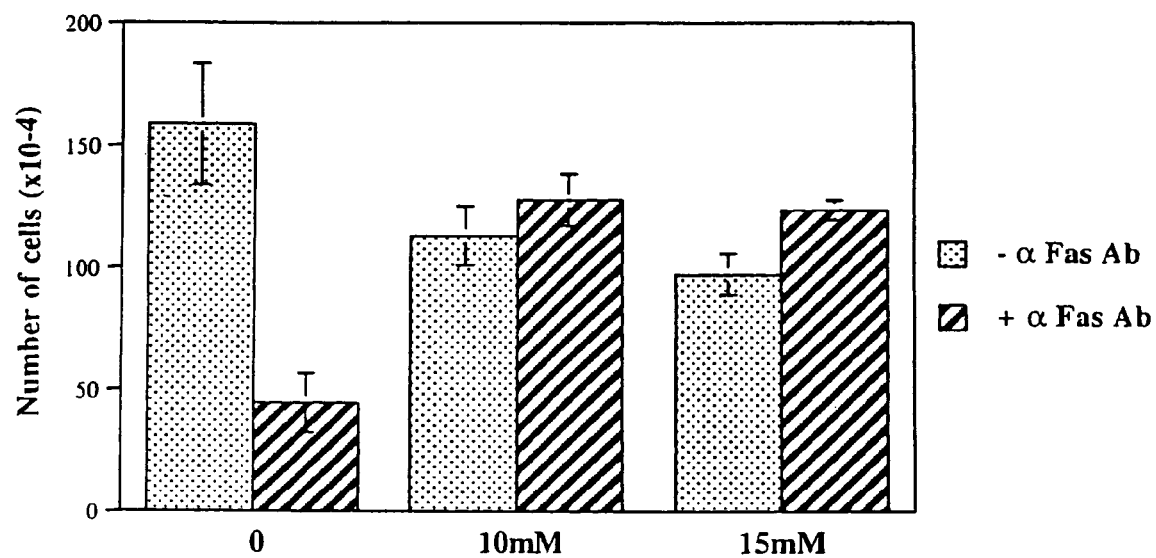

As shown in FIG. 5D, NAC strongly protects HeLa cells from Fas induced apoptosis as previously reported for microglia, neutrophils and T-cells.

Thus, by using AHM Nrf2 was identified as an inhibitor of Fas induced PCD in HeLa cells and this result was validated by genetic and pharmacological approaches. Interestingly, Ohtsubo et al has recently reported that Nrf2 is cleaved by caspase-3, producing a fragment that acts as a dominant negative fashion and is lethal. The mechanism underlying the mode of action of Nrf2 in regulating apoptosis deserves further investigation.

Figure 6A:
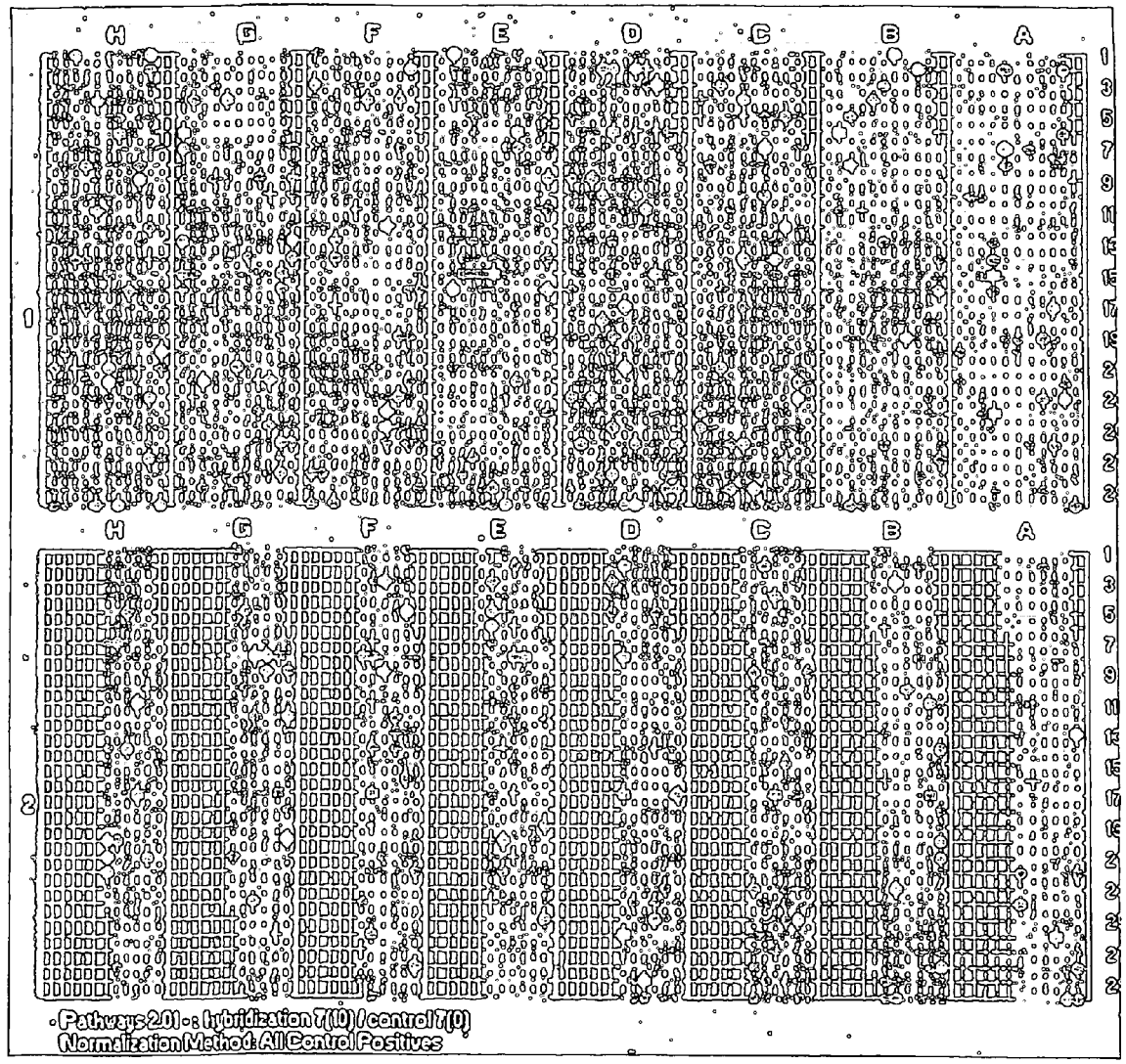
FIGS. 6A-B show the effect of the AHM method; A. shows "Function Profiling" generated by cDNA microarray analysis; B. shows the distribution of the differential abundance of cDNAs contained in the microarray.
Figure 6B:
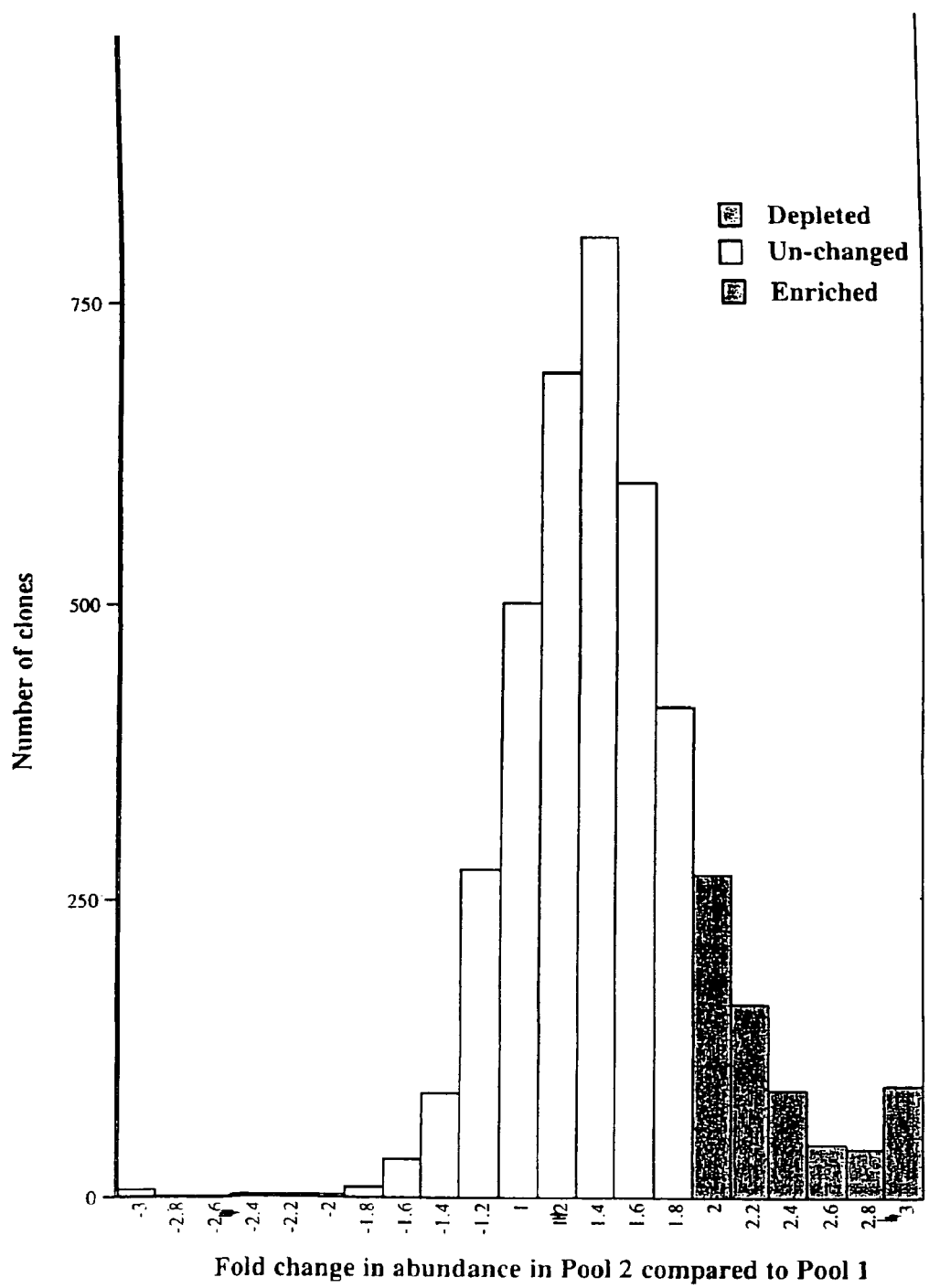

A technically simpler alternative to "function profiling" by subtraction is analysis of cDNA microarray. The relative abundance of cDNAs was measured in Pool 1 and in Pool 2 by radio-labeling each pool and hybridizing each of the probes to a cDNA microarray containing approximately 4,000 different known human genes. FIG. 6A is a pseudo colored image of the microarray filter representing for each cDNA spot the ratio of signal generated by hybridization to Pool 2 probe to that generated by Pool 1 probe. Dark green spots indicate cDNAs absent in Pool 2, representing "sensitizing" anti-sense cDNAs. The corresponding genes are predicted to be survival factors that inhibit Fas induced apoptosis. Dark red spots indicate cDNAs that are enriched in Pool 2. These genes are positive mediators of killing and their inactivation by anti-sense results in resistance to PCD. The abundance of such anti-sense cDNAs is therefore increased in Pool 2 that is comprised of cells that survived Fas induced apoptosis. Most of the spots are of intermediate color indicating only modest changes in abundance in Pool 2 relative to Pool 1. A histogram representation of the results is shown in FIG. 6B. As seen, the abundance of the majority of cDNAs is not changed. However, a small number of cDNAs are depleted from Pool 1 by 2 folds or more. A partial list of these genes is presented in Table A. As predicted, these genes include survival factors. For example, the most depleted cDNA (5.6-fold) corresponds to TNF receptor associated factor 6 that relays a strong survival signal via the activation of NFkB and AKT. In addition casein kinase 1 alpha and adenosine A3 receptor have been shown to be survival factors.

In summary, this is a novel powerful tool for identifying signaling inhibitors in human cells. Thus, a large gap in the genetic analyses of mammalian cells has now been filled. AHM can be broadly used to identify inhibitors of any given selectable pathway for the purposes of basic research or clinical applications. Moreover, since it does not require previous knowledge of any sequences, AHM can be employed as a high throughput method of gene discovery and "function profiling" as part of the ongoing effort of deciphering the human genome.

Materials and Methods:

AHM: HeLa cells ($10^6$ cells/100 mm plate) were transfected with 15 ug of anti-sense cDNA library in pTKO-1 (Deiss and Kimchi 1991) by Superfect reagent (Qiagen). Two days later cells were treated with 200 ug/ml Hygromycin B (Calbiochem-Novabiochem) for two weeks. $2.5 \times 10^6$ Hygromycin$^R$ cells were plated in a 150 mm plate 24 hours prior to treatment with 10 ng/ml anti-Fas antibody (clone CH-11, Kamiya Biomedical Company) (Pool 2). Five days post treatment approximately 30-40% of the cells were killed as estimated by microscopic examination. A parallel culture was grown in the absence of anti-Fas antibody (Pool 1). After five days, cells were washed twice with PBS, scraped off the plate and stored as pellets at −80°. 100 ul of frozen pellet were lysed by addition of 200 ul of solution P1, followed by 200 ul of solution P2. After the lysate sat on ice for 5 minutes 200 ul of solution P3 was added (Qiagen plasmid purification kit). Following 5 minutes incubation on ice, the lysate was centrifuged for 10 minutes at 15,000×g, the supernatant was mixed with an equal volume of isopropanol and centrifuged at 15,000×g for 10 minutes. The DNA pellet was rinsed with 70% ethanol and resuspended in 100 ul of water. The cDNA inserts were amplified by PCR in a 100 ul reaction containing: 1 ul DNA, 200 uM of dATP, dGTP, dCTP, dTTP; 10 mM Tris-HCl pH 9.0; 0.1% Triton X-100; 1.0 mM MgCl; 1 unit Taq DNA polymerase (Gibco BRL) and 500 ng each of primers. These primers are derived from the sequences that flank the cDNA insertion site in the pTKO-1 anti-sense expression vector. The primers are designed to restore a HindIII restriction site on the promoter proximal side of the cDNA and a BamHI site on the promoter distal side to conserve the orientation of the cDNA fragments upon their cloning in pTKO-1. The reaction was incubated 94° C. for 5 minutes; subjected to 25 cycles of: 94° C. for one minute, 58° C. for one minute and 72° C. for five minutes; followed by 72° C. for seven minutes. The PCR products were cleaved by BamHI and HindIII, purified (Wizard PCR Prep Kit, Promega) and used in subtraction (PCR-Select kit, Clontech). The driver for the subtraction was the product of the PCR reaction derived from the untreated cells (Pool 1) and the tester was derived from treated cells (Pool 2). The following modifications to the manufacturer's instructions were made: 1. The first step was IV F 3, since no cDNA synthesis is required. 2. The blunt ends adapters 1 and 2R were replaced with cohesive ends adapters.

Cohesive end adapters ligate more efficiently to the cDNA and permit the directional cloning of the cDNA inserts. 0.3 ug of the tester was used for adapter ligation. 3. The initial hybridization included 0.9 ug of the driver and 0.03 ug of the adapted ligated tester. The products of the subtraction were cleaved with BamHI and HindIII, purified and cloned into the pTKO-1 between BglII and HindIII sites. Individual clones were sequenced and transfected into HeLa cells.

Transfection and Bioassays: HeLa cells ($2 \times 10^6$ cells/100 mm plate) were plated 20 hours prior to transfection with either 17 ug of either anti-sense expressing vector or control vector harboring no cDNA insert, by calcium phosphate. Forty eight hours post transfection cells were treated with 200 ug/ml Hygromycin B (Calbiochem-Novabiochem) for two weeks. For bioassays, anti-sense transfected cells or control vector transfected cells ($1.6 \times 10^5$ cells/well in 6 wells plates) were plated 20-24 hours prior to the treatment with 200 ng/ml anti-Fas antibody (clone CH-11, Kamiya Biomedical Company). The number of viable, trypan blue (Gibco/BRL) excluding cells that remained attached to the plate following rinsing with PBS was counted 24 hours post treatment Western analysis: Anti-sense transfected cells or control vector transfected cells ($2.5 \times 10^6$ cells/150 mm plate) were plated 24 hours prior to treatment with 200 ng/ml anti-Fas antibody (clone CH-11, Kamiya Biomedical Company). 24 hours post treatment cells were washed with PBS and lysed in RIPA buffer (1% Nonidet P-40, 0.5%, sodium deoxycholate, 0.1% SDS, 1 mM PMSF, 2 mg/ml aprotonin and 2 mg/ml pepstatin in PBS). Samples containing 50 mg protein were separated by SDS-PAGE and transferred to nitrocellulose membranes. The immunoblots were probed with either anti-Nrf2 antibody (1:100, Santa Cruz, sc722) or anti-bFGF-2 antibody, (1:200, Santa Cruz, sc 079), incubated with goat anti rabbit conjugated to horseradish peroxidase (Pierce) followed by incubation with SuperSignal substrate (Pierce). Following autoradiography, the probes were stripped off (Amersham, ECL Western blotting protocols) and the membranes were hybridized with anti-actin antibody, (1:100, Sigma A4700 or A2066). The intensities of the bands were quantified by the National Institute of Health Image program.

Treatment with N-acetyl cysteine: HeLa cells ($8.3 \times 10^4$ cells/well in 6 wells plates) were plated 20-24 hours prior to treatment with various concentrations of NAC (Sigma/Aldrich,) in the presence or absence of 50 ng/ml anti-Fas antibody (clone CH-11, Kamiya Biomedical Company). The number of viable, trypan blue (Gibco/BRL) excluding cells that remained attached to the plate following rinsing with PBS was counted 5 days post treatment.

Treatment with Dicumarol: HeLa cells, $1.6 \times 10^5$ cells/well were plated in 6 wells plates. 20-24 hours later cells were treated with various concentrations of dicumarol (Sigma/Aldrich,) in 0.2 mM NaOH for 15 minutes prior to the addition of 200 ng/ml anti-Fas antibody (clone CH-11, Kamiya Biomedical Company). The number of viable, trypan blue (Gibco/BRL) excluding cells that remained attached to the plate following rinsing with PBS was counted 17 hours post treatment.

cDNA microarray analysis: Approximately 500 ng of the PCR products of Pool 1 and Pool 2 (same preparations that were used for the subtraction, before their cleavage by BamHI and HindIII) were labeled with 100 mCi of [$^{33}$P] dCTP (3000 Ci/mmole, ICN,) by the random primers DNA labeling system (Gibco/BRL), purified (Aershm/Pharmacia, ProbeQuant G50 micro columns) and individually hybridized to Human GeneFilters (GF211, Research Genetics). The filter was prehybridized for 40-60 minutes at 68° C. in ExpressHyb Hybridization solution (Clontech), followed by hybridization for 3-5 hours at 68° C. The filter was washed in 2×SSC, 0.05% SDS at room temperature 3-5 times for 10-15 minutes each time followed by 2 washes for 15 minutes each in 0.1×SSC, 0.1% SDS at 55° C. The image was generated by Molecular Dynamics phospho-imager. In between hybridizations, the probe was stripped off by adding boiling solution of 0.5% SDS and incubating at room temperature for 1 hour. Successful removal of probe was confirmed by phosphor-imager analysis. Images processing and calculation of the ratio of the signals of Pool 2 probe to Pool 1 probe were performed by Pathways II software (Research Genetics). All the spots that showed significant differential abundance were visually inspected.

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

REFERENCES

Altschul et al. (1990) Basic local alignment search tool. J. Mol. Biol., 215:403-410.

Braun et al. (1996) Molecular and Cellular Biology, (8):4623-4630.

Cregg et al. (1993) Recent Advances in the Expression of Foreign Genes in *Pichia pastoris*. Bio/Technology 11:905-910.

Deiss et al. (1996) Cathepsin D protease mediates programmed cell death induced by interferon-y, Fas/APO-1 and TNF-a. EMBO 15(15):3861-3870.

Deiss et al. (1995) Identification of a novel serine/threonine kinase and a novel 15-kD protein as potential mediators of the T interferon-induced cell death. Genes & Develop. 9:15-30.

Deiss and Kimchi (1991) A Genetic Tool Used to Identify Thioredoxin as a Mediator of a Growth Inhibitory Signal. Science 252:117-120.

Diatchenko et al. (1996) Proc. Natl. Acad. Sci. USA., 93:6025-6030.

Gilboa et al. (1986) Transfer and expression of cloned genes using retroviral vectors. BioTechniques 4(6):504-512.

Gubler and Hoffman (1983) Gene (Amst.) 25:263.

Gudkov et al. (1994) Cloning mammalian genes by expression selection of genetic suppressor elements: association of kinesin with drug resistance and cell immortalization. Proc. Natl. Acad. Sci. U.S.A.__, 91:3744-3748.

Hirt (1967) Selective extraction of polyoma DNA from infected mouse cell cultures. J. Mol. Biol., pp. 365-9.

Holzmayer et al. (1992) Isolation of dominant negative mutants and inhibitory antisense RNA sequences by expression selection of random DNA fragments. Nucleic Acids Res . . . , 20:711-717.

Izant and Weintraub (1984) Inhibition of thymidine kinase gene expression by anti-sense RNA: a molecular approach to genetic analysis. Cell, 36: 1007-1015.

Kissil et al. (1995) "Isolation of DAP3, a Novel Mediator of Interferon-T-induced Cell Death" J. Biol. Chem. 270(46): 27932-27936.

Levy-Strumpf et al. (1997) DAP-5, a novel homolog of eukaryotic translation initiation factor 4G isolated as a putative modulator of gamma interferon-induced programmed cell death. Mol. Cell. Biol._, 17: 1615-1625.

Li and Cohen (1996) Tsg101: A novel tumor susceptibility gene isolated by controlled homozygous functional knock-out of allelic loci in mammalian cells. Cell, 85:319-329.

Meissner et al. (1987) PNAS (USA) 84:4171.

Roninson et al. (1995) Genetic suppressor elements: new tools for molecular oncology—thirteenth Cornelius P. Rhoads Memorial Award Lecture. Cancer Res., 55:4023-4028.

Schena et al., 1995, Aiello et al., 1994, Shen et al., 1995, Bauer et al., 1993, Liang and Pardee, 1992, Liang and Pardee, 1995, Liang et al., 1993, Braun et al., 1995, Hubank and Schatz, 1994 Smith et al. (1995) genetic footprinting: a genomic strategy for determining a gene's function given its sequence. PNAS 92:6479-6489.

Su et al. (1993) LYAR, a novel nucleolar protein with zinc finger DNA-binding motifs, is involved in cell growth regulation. Genes Dev., 7:735-748. Schena et al. (1995) Science, 270:467-470.

Agrawal, 1996. Antisense oligonucleotides: towards clinical trials, TIBTECH, 14:376.

Calabretta, et al, 1996. Antisense strategies in the treatment of leukemias. Semin. Oncol. 23:78.

Crooke, 1995. Progress in antisense therapeutics, Hematol. Pathol. 2:59.

Felgner, 1997. Nonviral Strategeies for Gene Therapy. Scientific American. June, 1997, pgs 102-106.

Gewirtz, 1993. Oligodeoxynucleotide-based therapeutics for human leukemias, Stem Cells Dayt. 11:96.

Hanania, et al 1995. Recent advances in the application of gene therapy to human disease. Am. J. Med. 99:537.

Lefebvre-d'Hellencourt et al, 1995. Immunomodulation by cytokine antisense oligonucleotides. Eur. Cytokine Netw. 6:7.

Lev-Lehman et al., 1997. Antisense Oligomers in vitro and in vivo. In Antisense Therapeutics, A. Cohen and S. Smicek, eds (Plenum Press, New York) Loke et al, 1989. Characterization of oligonucleotide transport into living cells. PNAS USA 86:3474.

Wagner et al., 1996. Potent and selective inhibition of gene expression by an antisense heptanucleotide. Nature Biotechnology 14:840-844.

Wagner, 1994. Gene inhibition using antisense oligodeoxynucleotides. Nature 372:333.

Radhakrishnan et al., 1990. The automated synthesis of sulfur-containing oligodeoxyribonucleotides using 3H-1,2-Benzodithiol-3-One 1,1 Dioxide as a sulfur-transfer reagent. J. Org. Chem. 55:4693-4699.

What is claimed is:

1. A method of inducing apoptosis in a tumor cell of a subject comprising administering directly to the tumor cell an effective amount of an antisense compound or siRNA compound which hybridizes to a mRNA encoding Nrf2 so as to inhibit expression of the Nrf2 gene and induce apoptosis of the tumor cell.

2. The method according to claim 1, wherein the compound is an siRNA.

3. The method according to claim 1, wherein the compound is an antisense compound.

4. A method of sensitizing a tumor cell of a subject to chemotherapy associated with Fas induced apoptosis comprising administering directly to the tumor cell an effective amount of an antisense compound or an siRNA compound which hybridizes to a mRNA encoding Nrf2 so as to inhibit expression of the Nrf2 gene.

5. The method according to claim 4, wherein the compound is an antisense compound or an siRNA.

* * * * *

UNITED STATES PATENT AND TRADEMARK OFFICE
CERTIFICATE OF CORRECTION

| | | |
|---|---|---|
| PATENT NO. | : 7,749,977 B2 | Page 1 of 1 |
| APPLICATION NO. | : 11/586021 | |
| DATED | : July 6, 2010 | |
| INVENTOR(S) | : Fruma Yehiely, Louis Deiss and Paz Einat | |

It is certified that error appears in the above-identified patent and that said Letters Patent is hereby corrected as shown below:

On the title page, item (63), the fifth line to the seventh line, "filed as application No. PCT/US97/20989 on Nov. 12, 1997, now Pat. No. 6,057,111." should read --filed July 6, 1999, now U.S. Patent No. 6,057,111, issued May 2, 2000, which is a §371 national stage of PCT/US97/20989, filed Nov. 12, 1997.--

Signed and Sealed this
Nineteenth Day of April, 2011

David J. Kappos
*Director of the United States Patent and Trademark Office*